United States Patent
Vanderstraeten et al.

(10) Patent No.: US 11,673,003 B2
(45) Date of Patent: *Jun. 13, 2023

(54) DOSE ASPECTS OF RADIATION THERAPY PLANNING AND TREATMENT

(71) Applicants: Varian Medical Systems, Inc., Palo Alto, CA (US); Varian Medical Systems International AG., Cham (CH)

(72) Inventors: Reynald Vanderstraeten, Brussels (BE); Eric Abel, San Jose, CA (US); Christel Smith, Santa Barbara, CA (US); Anthony Magliari, Swansea, IL (US); Timo Koponen, Espoo (FI); Stanley Mansfield, Sunnyvale, CA (US); Charles Adelsheim, Mountain View, CA (US)

(73) Assignees: VARIAN MEDICAL SYSTEMS, INC., Palo Alto, CA (US); VARIAN MEDICAL SYSTEMS INTERNATIONAL AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,445

(22) Filed: Nov. 6, 2020

(65) Prior Publication Data
US 2021/0052917 A1 Feb. 25, 2021

Related U.S. Application Data

(63) Continuation of application No. 16/146,972, filed on Sep. 28, 2018, now Pat. No. 10,850,124, which is a
(Continued)

(51) Int. Cl.
*A61N 5/10* (2006.01)
*G16H 40/63* (2018.01)
(Continued)

(52) U.S. Cl.
CPC ......... *A61N 5/1031* (2013.01); *A61N 5/1038* (2013.01); *A61N 5/1045* (2013.01);
(Continued)

(58) Field of Classification Search
CPC . A61N 5/00; A61N 5/10; A61N 5/103; A61N 5/1031; A61N 5/1048;
(Continued)

(56) References Cited

U.S. PATENT DOCUMENTS

| | | | |
|---|---|---|---|
| 4,163,901 A | 8/1979 | Azam et al. | |
| 4,914,681 A | 4/1990 | Klingenbeck et al. | |

(Continued)

FOREIGN PATENT DOCUMENTS

| | | |
|---|---|---|
| CN | 104001270 | 8/2014 |
| CN | 106730407 | 5/2017 |

(Continued)

OTHER PUBLICATIONS

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

(Continued)

*Primary Examiner* — Jurie Yun
(74) *Attorney, Agent, or Firm* — Harness, Dickey & Pierce, P.L.C.

(57) ABSTRACT

Radiation treatment planning includes accessing values of parameters such as a number of beams to be directed into sub-volumes in a target, beam directions, and beam energies. Information that specifies limits for the radiation treatment plan are accessed. The limits include a limit on irradiation time for each sub-volume outside the target. Other limits can include a limit on irradiation time for each sub-volume in the target, a limit on dose rate for each sub-volume in the target, (Continued)

and a limit on dose rate for each sub-volume outside the target. The values of the parameters are adjusted until the irradiation time for each sub-volume outside the target satisfies the maximum limit on irradiation time.

20 Claims, 16 Drawing Sheets

Related U.S. Application Data continuation of application No. 15/657,094, filed on Jul. 21, 2017, now Pat. No. 10,092,774.

(51) Int. Cl.
| | | |
|---|---|---|
| *G16H 50/50* | (2018.01) | |
| *G16H 10/60* | (2018.01) | |
| *G16H 20/40* | (2018.01) | |
| *A61B 6/03* | (2006.01) | |

(52) U.S. Cl.
CPC ............ *G16H 10/60* (2018.01); *G16H 20/40* (2018.01); *G16H 40/63* (2018.01); *G16H 50/50* (2018.01); *A61B 6/032* (2013.01); *A61N 5/1043* (2013.01); *A61N 5/1069* (2013.01); *A61N 5/1071* (2013.01)

(58) Field of Classification Search
CPC .. A61N 5/1064; A61N 5/1065; A61N 5/1038; A61N 5/1045; A61N 5/1043; A61N 5/1069; A61N 5/1071; A61N 2005/0626; A61N 2005/0627; A61N 2005/1041; G16H 20/40; A61B 6/03; A61B 6/032; G06F 19/00
See application file for complete search history.

(56) References Cited

U.S. PATENT DOCUMENTS

| | | |
|---|---|---|
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |

(56) References Cited

U.S. PATENT DOCUMENTS

| | | | |
|---|---|---|---|
| 10,758,746 B2 | 9/2020 | Kwak et al. | |
| 10,850,124 B2 * | 12/2020 | Vanderstraeten | G16H 10/60 |
| 10,870,018 B2 | 12/2020 | Bartkoski et al. | |
| 2007/0287878 A1 | 12/2007 | Fantini et al. | |
| 2008/0023644 A1 | 1/2008 | Pedroni | |
| 2009/0063110 A1 | 3/2009 | Failla et al. | |
| 2009/0287467 A1 | 11/2009 | Sparks et al. | |
| 2010/0119032 A1 | 5/2010 | Yan et al. | |
| 2010/0177870 A1 | 7/2010 | Nord et al. | |
| 2010/0178245 A1 | 7/2010 | Arnsdorf et al. | |
| 2010/0260317 A1 | 10/2010 | Chang et al. | |
| 2011/0006224 A1 | 1/2011 | Maltz et al. | |
| 2011/0091015 A1 | 4/2011 | Yu et al. | |
| 2011/0135058 A1 | 6/2011 | Sgouros et al. | |
| 2012/0076271 A1 | 3/2012 | Yan et al. | |
| 2012/0157746 A1 | 6/2012 | Meltsner et al. | |
| 2012/0171745 A1 | 7/2012 | Itoh | |
| 2012/0197058 A1 | 8/2012 | Shukla et al. | |
| 2013/0116929 A1 | 5/2013 | Carlton et al. | |
| 2013/0150922 A1 | 6/2013 | Butson et al. | |
| 2013/0177641 A1 | 7/2013 | Ghoroghchian | |
| 2013/0231516 A1 | 9/2013 | Loo et al. | |
| 2014/0177807 A1 | 6/2014 | Lewellen et al. | |
| 2014/0185776 A1 | 7/2014 | Li et al. | |
| 2014/0206926 A1 | 7/2014 | Van Der Laarse | |
| 2014/0275706 A1 | 9/2014 | Dean et al. | |
| 2014/0369476 A1 | 12/2014 | Harding | |
| 2015/0011817 A1 | 1/2015 | Feng | |
| 2015/0202464 A1 | 7/2015 | Brand et al. | |
| 2015/0306423 A1 | 10/2015 | Bharat et al. | |
| 2016/0279444 A1 | 9/2016 | Schlosser | |
| 2016/0310764 A1 | 10/2016 | Bharadwaj et al. | |
| 2017/0189721 A1 | 7/2017 | Sumanaweera et al. | |
| 2017/0203129 A1 | 7/2017 | Dessy | |
| 2017/0281973 A1 | 10/2017 | Allen et al. | |
| 2018/0021594 A1 | 1/2018 | Papp et al. | |
| 2018/0043183 A1 | 2/2018 | Sheng et al. | |
| 2018/0056090 A1 | 3/2018 | Jordan et al. | |
| 2018/0099154 A1 | 4/2018 | Prieels | |
| 2018/0099155 A1 | 4/2018 | Prieels et al. | |
| 2018/0099159 A1 | 4/2018 | Forton et al. | |
| 2018/0154183 A1 | 6/2018 | Sahadevan | |
| 2018/0197303 A1 | 7/2018 | Jordan et al. | |
| 2018/0207425 A1 | 7/2018 | Carlton et al. | |
| 2018/0236268 A1 | 8/2018 | Zwart et al. | |
| 2019/0022407 A1 | 1/2019 | Abel et al. | |
| 2019/0022422 A1 | 1/2019 | Trail et al. | |
| 2019/0054315 A1 | 2/2019 | Isola et al. | |
| 2019/0070435 A1 | 3/2019 | Joe Anto et al. | |
| 2019/0168027 A1 | 6/2019 | Smith et al. | |
| 2019/0255361 A1 | 8/2019 | Mansfield | |
| 2019/0299027 A1 | 10/2019 | Fujii et al. | |
| 2019/0299029 A1 | 10/2019 | Inoue | |
| 2019/0351259 A1 | 11/2019 | Lee et al. | |
| 2020/0001118 A1 | 1/2020 | Snider, III et al. | |
| 2020/0022248 A1 | 1/2020 | Yi et al. | |
| 2020/0030633 A1 | 1/2020 | Van Heteren et al. | |
| 2020/0035438 A1 | 1/2020 | Star-Lack et al. | |
| 2020/0069818 A1 | 3/2020 | Jaskula-Ranga et al. | |
| 2020/0164224 A1 | 5/2020 | Vanderstraten et al. | |
| 2020/0178890 A1 | 6/2020 | Otto | |
| 2020/0197730 A1 | 6/2020 | Safavi-Naeini et al. | |
| 2020/0254279 A1 | 8/2020 | Ohishi | |
| 2020/0269068 A1 | 8/2020 | Abel et al. | |
| 2020/0276456 A1 | 9/2020 | Swerdloff | |
| 2020/0282234 A1 | 9/2020 | Folkerts et al. | |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259 bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "Flash optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H MacKeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Fherapy," Technology in Cancer Research & Treatment, vol. 2, No. 5, Oct. 2003, p. 437-444, Adenine Press.

(56) References Cited

OTHER PUBLICATIONS

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus on the Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 3, 20160, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between ormal and tumor tissue in mice," Science Translational Medicine, Jul. 16, 2014, vol. 6, Issue 245, 245ra93, American Association for the Advancement of Science, DOI: 10.1126/scitranslmed.3008973.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH adiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Dncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: Flash: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy,"

(56) References Cited

OTHER PUBLICATIONS

Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr.20170628.

John R. Fischer, "PMB launches FLASH radiotherapy system for use in clinical trials," Healthcare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xIL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects of High Energy Radiation and Ultra High Dose Rates," UMEA University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for eady and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Repod 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

* cited by examiner

DOSE ASPECTS OF RADIATION THERAPY PLANNING AND TREATMENT

RELATED U.S. APPLICATIONS

This application is a continuation of the application with Ser. No. 16/146,972, entitled "Dose Aspects of Radiation Therapy Planning and Treatment," by R. Vanderstraeten et al., filed Sep. 28, 2018, which is a continuation of the application with Ser. No. 15/657,094, entitled "Dose Aspects of Radiation Therapy Planning and Treatment," by R. Vanderstraeten et al., filed Jul. 21, 2017, now U.S. Pat. No. 10,092,774, both of which are hereby incorporated by reference in their entireties.

This application is related to U.S. application Ser. No. 15/657,052, by R. Vanderstraeten et al., entitled "Geometric Aspects of Radiation Therapy Planning and Treatment," filed Jul. 21, 2017, now U.S. Pat. No. 10,549,117, hereby incorporated by reference in its entirety.

BACKGROUND

The use of radiation therapy to treat cancer is well known. Typically, radiation therapy involves directing a beam of high energy proton, photon, ion, or electron radiation ("therapeutic radiation") into a target or target volume (e.g., a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the target while minimizing exposure of surrounding normal, healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. FLASH RT thus introduces important constraints that are not considered in or achieved with conventional radiation treatment planning.

SUMMARY

In intensity modulated radiation therapy (IMRT) such as intensity modulated particle therapy (IMPT), beam intensity is varied across each treatment region (target) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Embodiments according to the present invention provide an improved method of radiation treatment planning, and improved radiation treatment based on such planning, for FLASH radiation therapy (FLASH RT). In embodiments, values of parameters such as a number of beams to be directed into and across sub-volumes in a target, directions of the beams (e.g., gantry angles relative to the patient or target, or nozzle directions relative to the patient or target), and beam energies for the beams are accessed. The directions are determined such that an amount of overlap of the beams' paths outside the target is minimized or such that the paths of the beams do not overlap at all outside the target. The beams may or may not overlap within the target. The beams can be proton beams, electron beams, photon beams, ion beams, or atom nuclei beams (e.g., carbon, helium, and lithium).

In embodiments, radiation treatment planning includes accessing values of parameters such as a number of beams to be directed into sub-volumes in a target, beam directions, and beam energies. Information that specifies limits for the radiation treatment plan is accessed. In embodiments, the limits are based on a dose threshold, and include a maximum limit on irradiation time for each sub-volume outside the target. The dose threshold may be dependent on tissue type. Other limits can include a maximum limit on irradiation time for each sub-volume in the target, a minimum limit on dose rate for each sub-volume in the target, and a minimum limit on dose rate for each sub-volume outside the target. In embodiments, the values of the parameters are adjusted until the irradiation time for each sub-volume outside the target satisfies the maximum limit on irradiation time.

In embodiments, the portion of each beam within the target is represented as a respective set of longitudinal beam regions. Each beam region in each set has a value corresponding to a calculated amount of dose to be delivered by the beam region. For proton beams or ion beams that have a Bragg peak, the value assigned to the beam region that corresponds to the Bragg peak of the beam is greater than other values assigned to other beam regions. If two or more beams overlap within the target, then one or more sub-volumes within the target will receive doses from more than one beam. For each sub-volume in the target, the values assigned to the beam regions that overlap in the sub-volume are added together to determine a total value for the sub-volume; if only one beam region reaches a particular sub-volume, then the total value is the value for that beam region. The parameters that affect the calculated amounts of dose to be delivered by the beam regions are adjusted until the total values for the sub-volumes are within a specified range of each other or are the same, thereby indicating that the dose to be delivered across the target is satisfactorily uniform.

In embodiments, a maximum energy for each beam is specified, and an energy for each of the beam segments in the beam is determined as a percentage (100 percent or less) or equivalent fraction of that beam's maximum energy. In embodiments, beams that have paths that overlap another beam path outside the target are identified and the beam intensities for the beam segments of those beams are reduced in the dose calculations. In one or more of these embodiments, the beam intensities for beam segments of an overlapping beam are weighted according to how many other beams are overlapped by that beam.

In embodiments, when performing a dose calculation for a sub-volume that is outside the target, a value for a dose calculation factor for the outside-the-target sub-volume is accessed. The value for the dose calculation factor is based on how many beams are received by the outside-the-target sub-volume. The value of the dose calculation factor is applied to the dose calculated for the outside-the-target sub-volume to account for the tissue-sparing effects of FLASH RT on normal tissue.

In embodiments, the number of times (how many times) each beam can be turned on is determined, and the amount of time (for how long) a beam can be turned on each time the beam is turned on is also determined, such that the total amount of time that a beam is turned on does not exceed a maximum limit for that beam. In this manner, a total amount of time each sub-volume outside the target is irradiated by one beam (turned on one or more times) or by multiple beams (each beam turned on one or more times) does not exceed a maximum limit and, therefore, a total amount of dose delivered to each sub-volume outside the target does not exceed a maximum limit.

In embodiments according to the invention, instead of the conventional approach of specifying a maximum dose rate and a minimum treatment time in the treatment plan, limits are specified for a maximum irradiation time for each sub-volume in the target, a maximum irradiation time for each sub-volume outside the target, a minimum dose rate for each sub-volume in the target, and a minimum dose rate for each sub-volume outside the target. As noted above, FLASH RT entails delivering a relatively high radiation dose to a target within a short period of time. For example, each beam can deliver at least four grays (Gy) in less than one second, and may deliver as much as 20 Gy or 50 Gy or more in less than one second. In embodiments, the dose threshold is dependent on tissue type.

Embodiments according to the invention improve radiation treatment planning and the treatment itself by expanding FLASH RT to a wider variety of treatment platforms and target sites (e.g., tumors). Treatment plans generated as described herein are superior for sparing normal tissue from radiation in comparison to conventional techniques for FLASH dose rates and even non-FLASH dose rates by reducing, if not minimizing, the magnitude of the dose, and in some cases the integrated dose, to normal tissue (outside the target) by design. When used with FLASH dose rates, management of patient motion is simplified. Treatment planning, while still a complex task, is simplified relative to conventional planning.

In summary, embodiments according to this disclosure pertain to generating and implementing a treatment plan that is the most effective (relative to other plans) and with the least (or most acceptable) side effects (e.g., the lowest dose outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans, fewer computational resources are needed and consumed, meaning also that computer resources are freed up to perform other tasks.

In addition to IMRT and IMPT, embodiments according to the invention can be used in spatially fractionated radiation therapy including high-dose spatially fractionated grid radiation therapy and microbeam radiation therapy.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
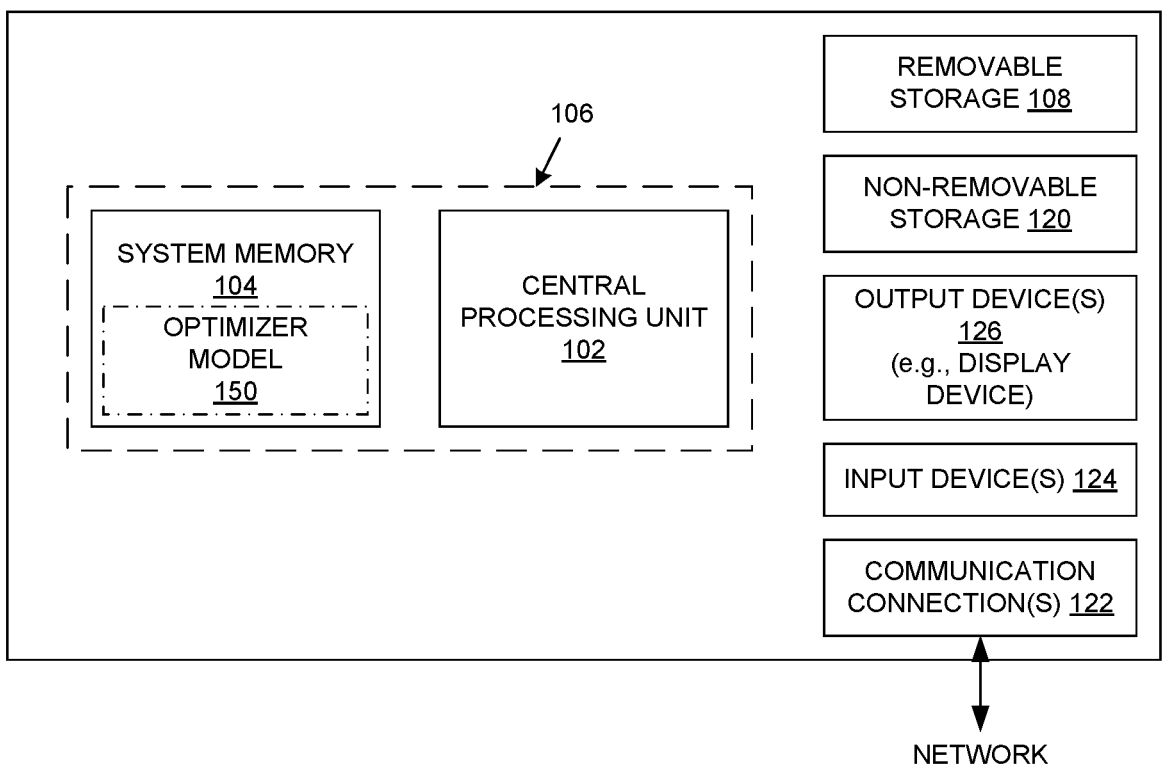
FIG. 1 is a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "representing," "applying," "adding," "multiplying," "adjusting," "calculating," "predicting," "weighting," "assigning," "using," "identifying," "reducing," "downloading," "reading," "computing," "storing," or the like, refer to actions and processes (e.g., the flowcharts of FIGS. 5, 7B, 9, 11, 12, and 13) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein (e.g., FIGS. 5, 7B, 9, 11, 12, and 13) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
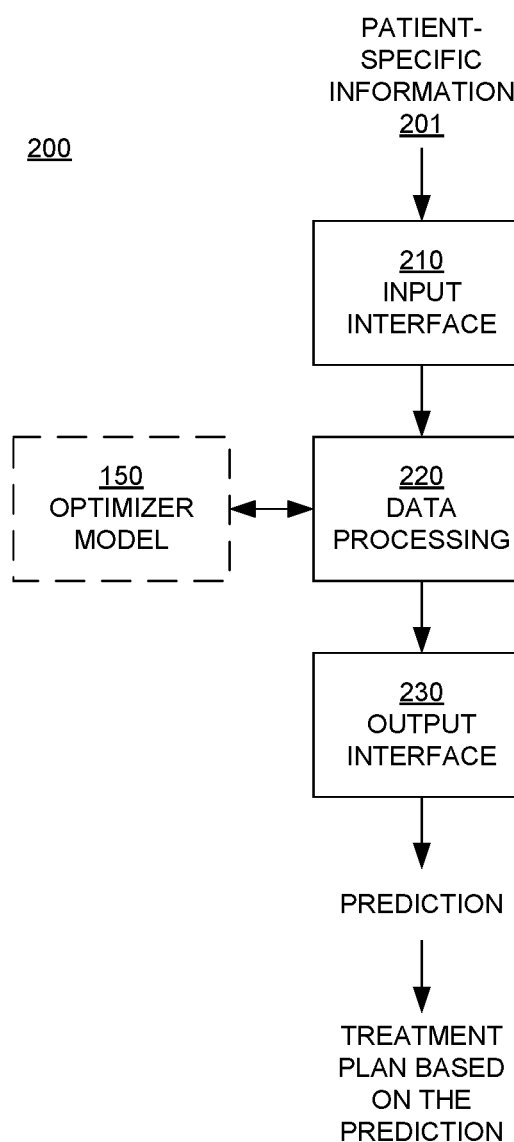
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
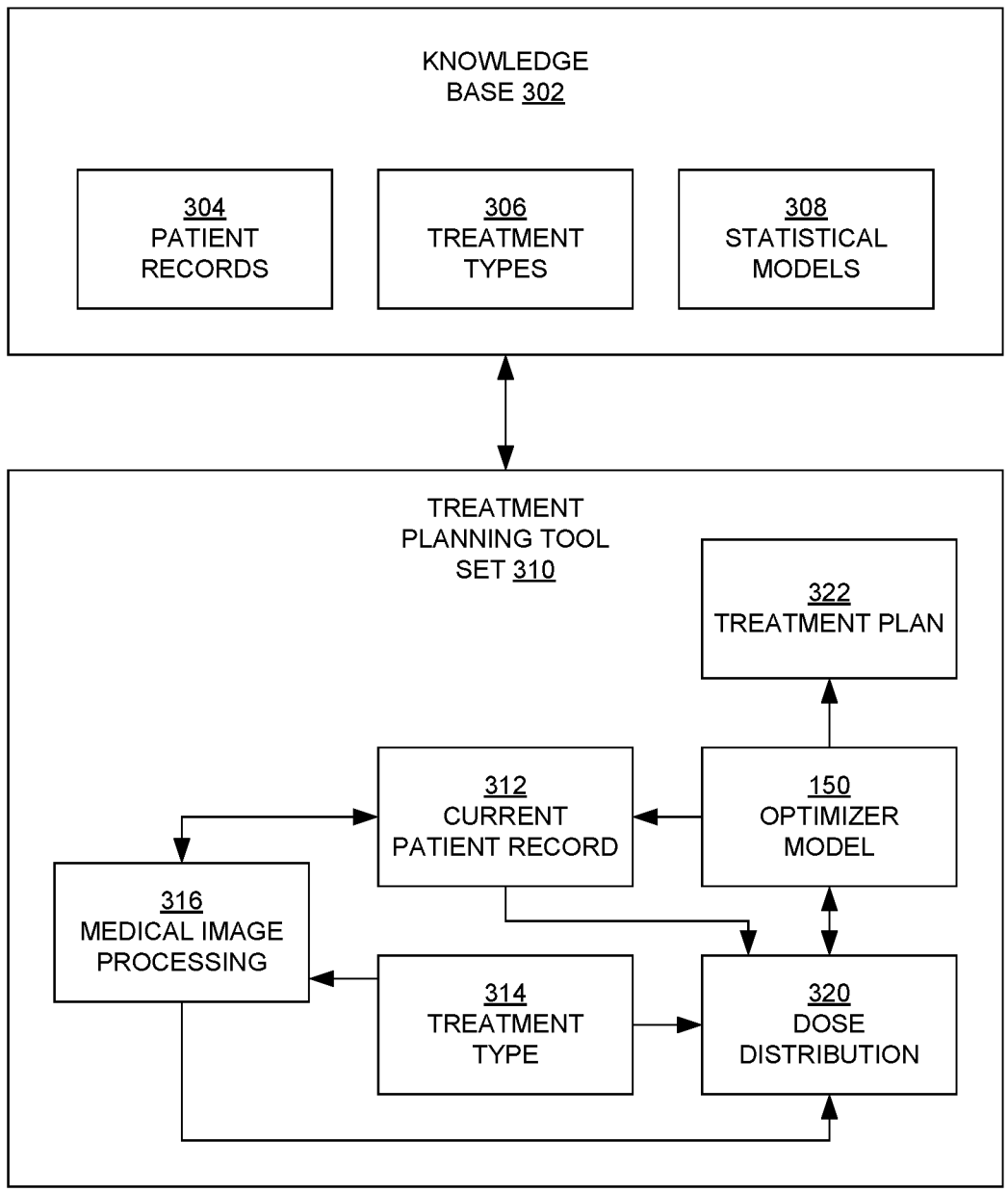
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography or magnetic resonance imaging) to form a three-dimensional (3D) image using the medical images in the current patient record 312. Dose distribution maps are calculated by the dose distribution module 320, which may utilize the optimizer model 150.

In embodiments according to the present invention, the optimizer model 150 uses a dose prediction model to help shape the dose distribution. The optimizer model 150 can provide, for example, a 3D dose distribution, fluences, and associated dose-volume histograms for the current patient.

Figure 4A:
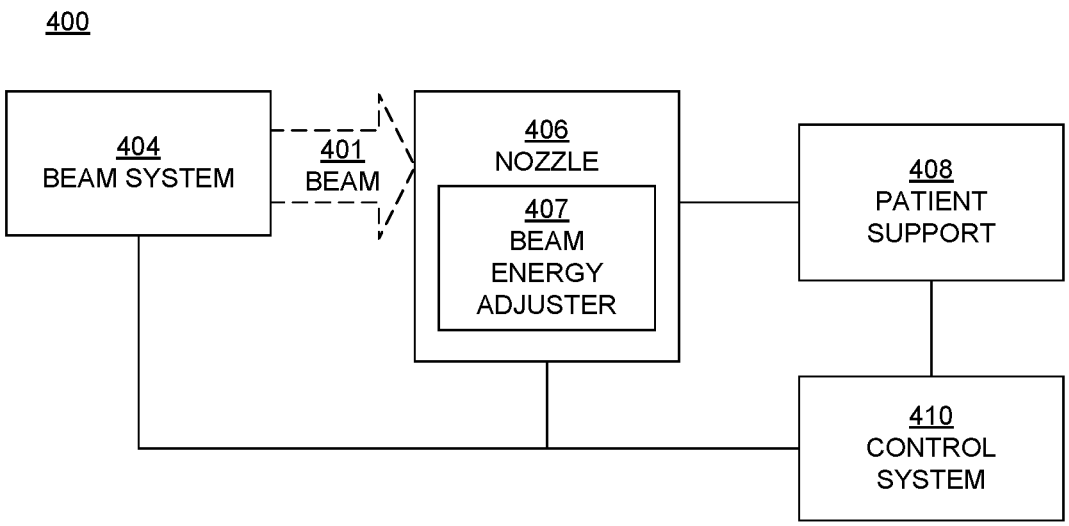
FIG. 4A is a block diagram showing selected components of a radiation therapy system upon which embodiments according to the present invention can be implemented.

FIG. 4A is a block diagram showing selected components of a radiation therapy system 400 upon which embodiments according to the present invention can be implemented. In the example of FIG. 4A, the system 400 includes a beam system 404 and a nozzle 406.

The beam system 404 generates and transports a beam 401 to the nozzle 406. The beam 401 can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam system in a direction toward and into the nozzle 406. In embodiments, the radiation therapy system may include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 is used to aim the beam toward various locations (a target) within an object (e.g., a patient) supported on the patient support device 408 (e.g., a chair or table) in a treatment room. A target may be an organ, a portion of an organ (e.g., a volume or region within the organ), a tumor, diseased tissue, or a patient outline.

The nozzle 406 may be mounted on or a part of a gantry (FIGS. 4B, 4C, and 4D) that can be moved relative to the patient support device 408, which may also be moveable. In embodiments, the beam system 404 is also mounted on or is a part of the gantry; in another embodiment, the beam system is separate from (but in communication with) the gantry.

The control system 410 of FIG. 4A receives and implements a prescribed treatment plan. In embodiments, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and/or shape of the beam, according to data it receives and according to the prescribed treatment plan.

As noted above, the beam entering the nozzle 406 has a specified energy. Thus, in embodiments according to the present disclosure, the nozzle 406 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster can control the location of the Bragg peak in the target. In various embodiments, the beam energy adjuster 407 includes a range modulator, a range shifter, or both a range modulator and a range shifter. That is, when the term "beam energy adjuster" is used, then the element being discussed may be a range modulator, a range shifter, or both a range modulator and a range shifter. Examples of a beam energy adjuster for proton beams and ion beams are disclosed in the co-pending patent application, U.S. application Ser. No. 15/089,330, entitled "Radiation Therapy Systems and Methods" (as-filed), now U.S. Pat. No. 9,855,445; however, the invention is not so limited.

Figure 4B:
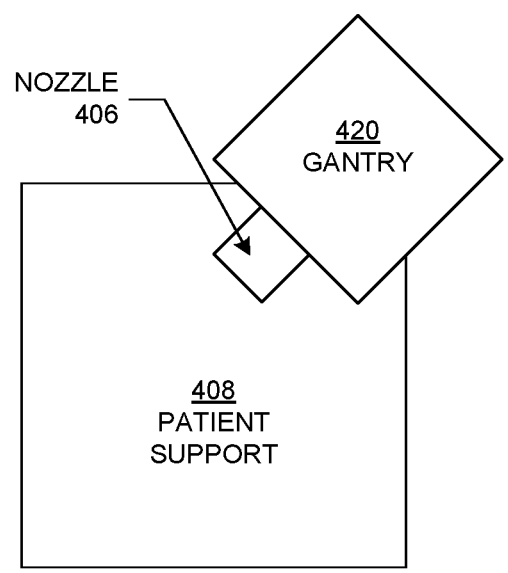
FIG. 4B is a block diagram illustrating a non-coplanar arrangement of a gantry and nozzle relative to a patient support device in embodiments according to the invention.
Figure 4C:
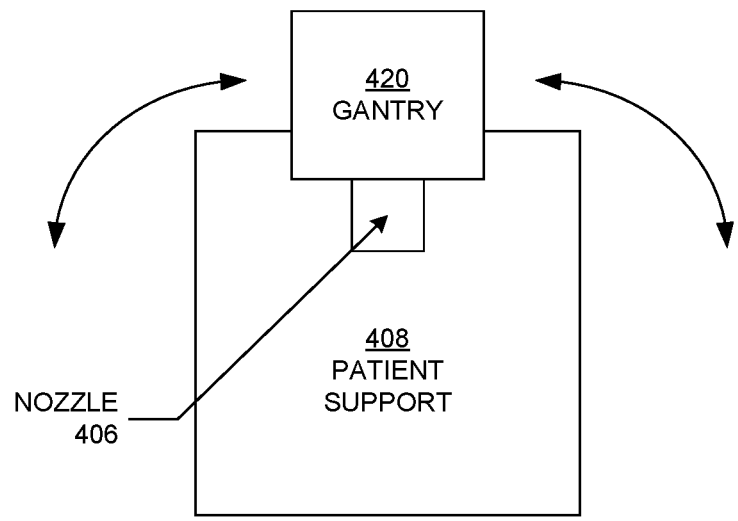
FIG. 4C is a block diagram illustrating a coplanar arrangement of a gantry and nozzle relative to a patient support device in embodiments according to the invention.
Figure 4D:
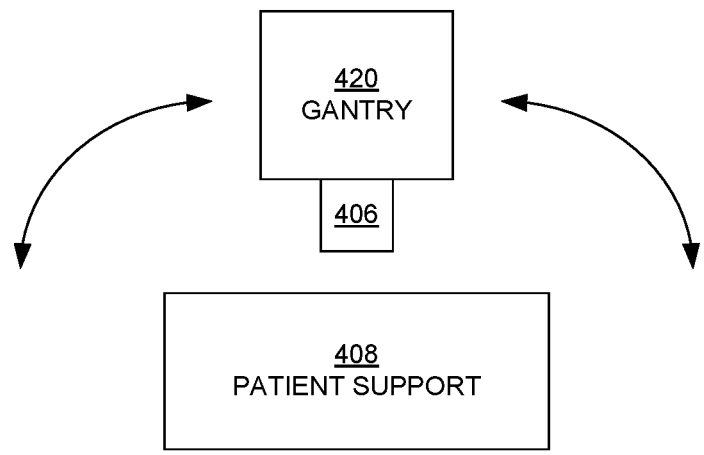
FIG. 4D is a block diagram illustrating movement of a gantry and nozzle around a patient support device in embodiments according to the invention.

FIG. 4B is a block diagram illustrating a non-coplanar arrangement of a gantry 420 and nozzle 406 relative to a patient support device 408 in embodiments according to the invention. FIG. 4C is a block diagram illustrating a coplanar arrangement of a gantry 420 and nozzle 406 relative to a patient support device 408 and also illustrating movement of the gantry and nozzle around the patient support device in embodiments according to the invention. FIG. 4D is a block diagram illustrating movement of the gantry 420 and nozzle 406 around the patient support device 408 in embodiments according to the invention. This movement can occur in either the non-coplanar arrangement or the coplanar arrangement.

Figure 5:
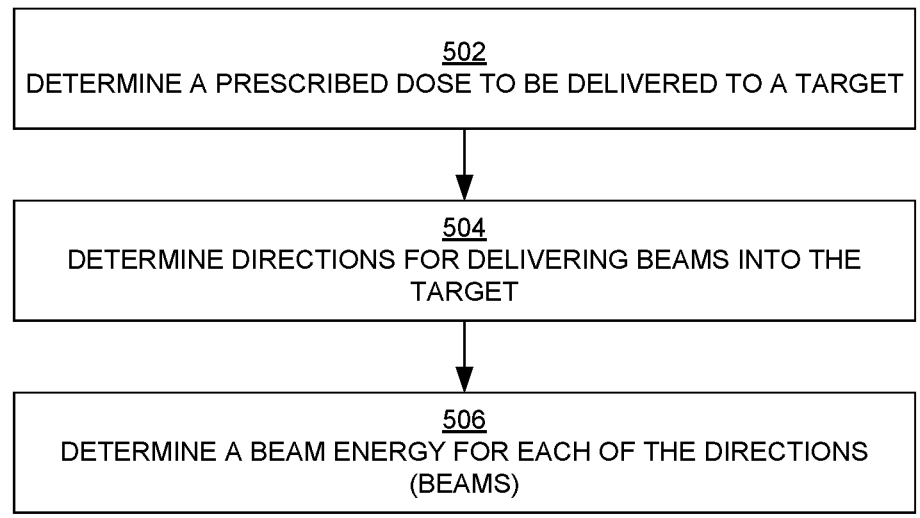
FIG. 5 is a flowchart of an example of computer-implemented operations for generating a radiation treatment plan in embodiments according to the present invention.

FIG. 5 is a flowchart 500 of an example of computer-implemented operations for generating a radiation treatment plan in embodiments according to the present invention. The flowchart 500 can be implemented as computer-executable instructions (e.g., the optimizer model 150 of FIG. 1) residing on some form of computer-readable storage medium (e.g., using the computing system 100 of FIG. 1).

In intensity modulated radiation therapy (IMRT) such as intensity modulated particle therapy (IMPT), beam intensity is varied across each treatment region (target) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

In block 502 of FIG. 5, a prescribed dose to be delivered into and across the target is determined. Each portion of the target can be represented by at least one 3D element known as a voxel; a portion may include more than one voxel. A portion of a target or a voxel may also be referred to herein as a sub-volume; a sub-volume may include one or more portions or one or more voxels. As will be described in detail below, each portion or voxel may receive radiation from one or more beams delivered from different directions. The prescribed dose defines, for example, a dose value, or a minimum dose value and a maximum dose value, for each portion or voxel of the target. In embodiments, the prescribed dose is the same for all portions (sub-volumes or voxels) of the target, such that a uniform dose is prescribed for the entire target.

In block 504, directions (e.g., gantry angles relative to the patient or target, or nozzle directions relative to the patient or target) for delivering beams into the target are determined. The beams can be proton beams, electron beams, photon beams, ion beams, or atom nuclei beams. The operation of determining beam directions can include determining the number of beams (the number of directions from which beams are to be delivered). The beams' paths may or may not overlap within the target, and may or may not overlap outside the target. In general, when generating the radiation treatment plan, one goal is to determine beam paths that minimize the irradiation time of each sub-volume or voxel of the tissue outside the target. Ideally, each sub-volume or voxel outside the target is intersected, at most, by only a single beam. If some overlap between beam paths is permitted, then ideally each sub-volume or voxel outside the target is intersected by not more than two beams, with most intersected by only a single beam. In embodiments, as one means of achieving the aforementioned goal, the beam directions are determined such that the total amount of overlap between the beams' paths is minimized outside the target. In one such embodiment, the directions are determined such that the paths of the beams overlap within the target and such that the total amount of overlap of the beams' paths outside the target is less than the total amount of the overlap of the beams' paths within the target. In another such embodiment, the directions are determined so that the paths of the beams do not overlap at all outside the target. The beams' paths can lie within the same plane, or they can be in different planes. Additional information is provided in conjunction with FIGS. 6A, 6B, 6C, and 6D.

Any number of other factors may be considered when determining the beam directions. These factors may include the shape and size (e.g., height H and width W, or diameter) of the beam in the beam's eye view (see FIG. 7A). These factors may also include, for example, the amount or type of healthy tissue that a beam will be traveling through. That is, one beam direction may be more favorable than another if it travels a shorter distance through healthy tissue or avoids passing through a vital organ and may be weighted accordingly.

In block 506 of FIG. 5, a beam energy or intensity is determined for each of the directions (for each of the beams). The beam energy or intensity for each direction is determined such that the predicted or calculated cumulative doses (e.g., doses calculated using the optimizer model 150 of FIG. 1) at locations inside the target satisfy the prescribed dose as defined in block 502. As noted, beam paths may or may not overlap in the target; if the beams' paths overlap in the target, then the beam energy or intensity for each direction is determined such that the predicted or calculated cumulative doses (e.g., doses calculated using the optimizer model 150 of FIG. 1) at locations inside the target where the beams' paths overlap satisfy the prescribed dose as defined in block 502. In embodiments, a beam includes a number of beam segments or beamlets. In one or more such embodiments, a maximum energy (e.g., 80 MeV) for the beam is specified, and an energy for each of the beam segments is determined as a percentage (100 percent or less) or equivalent fraction of the maximum beam energy. In general, beams can have the same energy or different energies, and each beam can have a range of energies. Thus, different energies or intensities can be delivered in different directions, and different energies or intensities can be delivered in each direction. Additional information is provided in conjunction with FIGS. 7A, 7B, 7C, and 7D.

While the operations in blocks 502, 504, and 506 of FIG. 5 are presented as occurring in series and in a certain order, the present invention is not so limited. The operations may be performed in a different order and/or in parallel, and they may also be performed in an iterative manner, as the number of beams (and accordingly, the number of directions), the beam directions, and the beam energies or intensities (and/or beam segment energies or intensities) used to deliver the prescribed dose are interrelated. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computing system 100 (FIG. 1) for radiation treatment planning as disclosed herein is important.

The discussion to follow refers to beams, targets, doses, and other elements or values. The discussion below is in the context of modeled elements and calculated values in the treatment planning tool set 310 and the optimizer model 150 (FIG. 3), unless otherwise noted or made clear in the discussion.

Figure 6A:
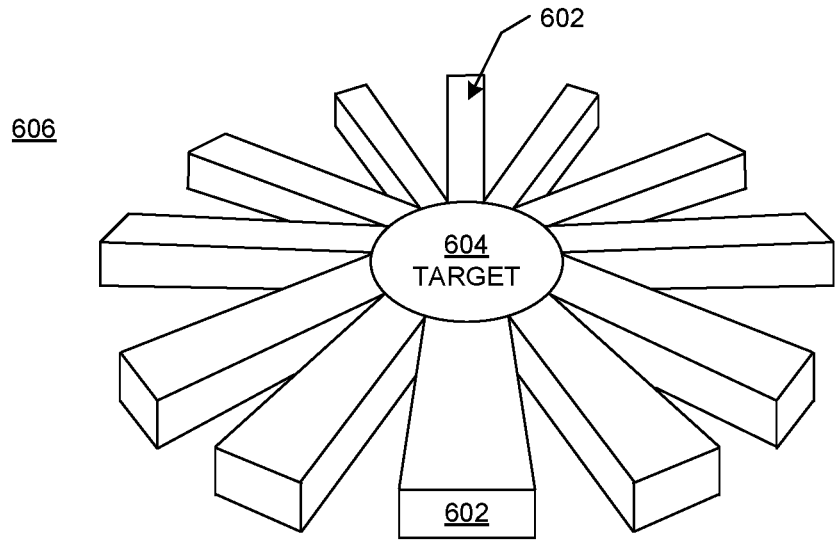
FIG. 6A illustrates a perspective view of an example of a beam geometry in embodiments according to the invention.

FIG. 6A illustrates a perspective view of an example of a beam geometry in embodiments according to the invention. In the example of FIG. 6A, the beams (exemplified by beam 602) are in the same plane. The beams can be proton beams, electron beams, photon beams, ion beams, or atom nuclei beams. Each beam can deliver a relatively high dose in a relatively short period of time. For example, in embodiments, each beam can deliver doses sufficient for FLASH RT (e.g., at least four (4) grays (Gy) in less than one second, and as much as 20 Gy or 50 Gy or more in less than one second). In embodiments, the range is 0.01-500 Gy. As described herein, each beam can include one or more beam segments or beam lets. In this example, the beams' paths overlap only within the target 604, and do not overlap outside the target in the surrounding tissue 606.

In the example of FIG. 6A, the beam 602 (for example) is illustrated as passing completely through the target 604. For beams that have a Bragg peak (e.g., proton beams and ion beams), the ranges of the beams can be controlled so that the beam does not pass completely through the target, as will be described further below.

Although multiple beams are shown in FIG. 6A, this does not mean that all beams are necessarily delivered at the same time or in overlapping time periods, although they can be. The number of beams delivered at any one time depends on the number of gantries or nozzles in the radiation treatment system (e.g., the radiation treatment system 400 of FIG. 4A) and on the treatment plan.

Figure 6B:
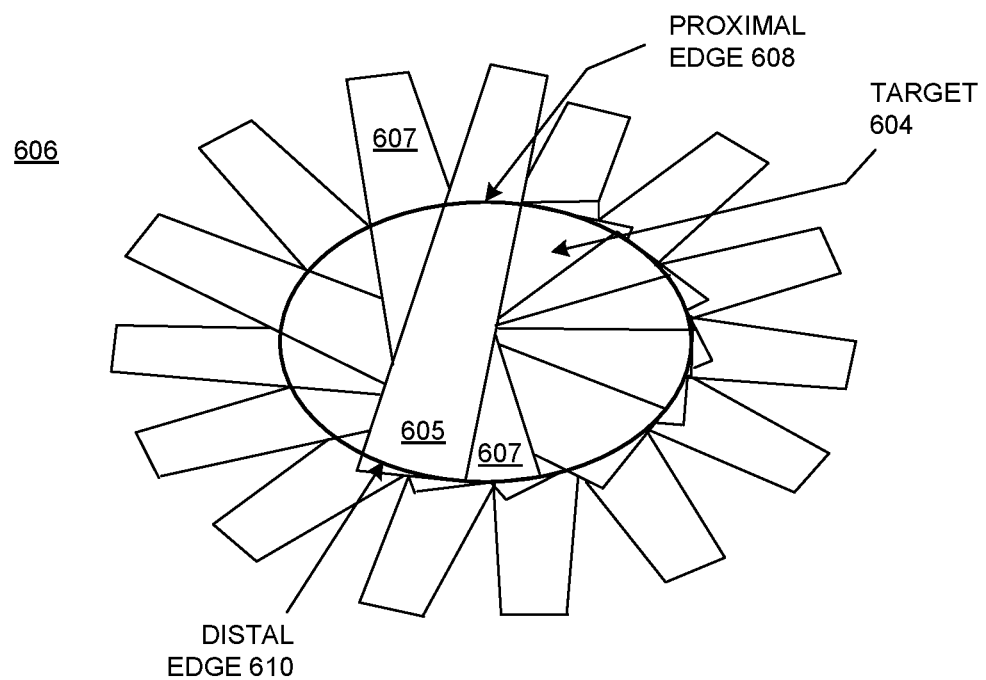
FIG. 6B illustrates a cross-sectional view of an example of a beam geometry in embodiments according to the invention.

FIG. 6B illustrates a cross-sectional view of an example of a beam geometry in embodiments according to the invention. In this example, the beams (exemplified by beams 605 and 606) overlap only within the target and are in the same plane. The figure depicts the beams in overlapping fashion to demonstrate that each portion of the target 604 receives a dose of radiation. The beams can be proton beams, electron beams, photon beams, ion beams, or atom nuclei beams. In the example of FIG. 6B, the beams are illustrated as not extending beyond the distal edge of the target 604 (as would be the case for proton or ion beams, for example); however, the invention is not so limited. Each beam can deliver a relatively high dose in a relatively short period of time. For example, each beam can deliver doses sufficient for FLASH RT.

As will be discussed further in conjunction with FIG. 7C, for implementations in which the beams have a Bragg peak, such as a proton beam or an ion beam, the dose delivered by a beam (or beam segment) is not necessarily uniform along the entire length of the beam path through the target 604. Thus, for example, for a proton or ion beam, the dose delivered by the beam 605 at the proximal portion (or edge) 608 of the target 604 may be different from (e.g., less than) the dose delivered by that beam at the distal portion (or edge) 610 of the target (here, proximal and distal are with reference to the source of the beam 605). The same can be said for each proton or ion beam.

The dose delivered to each portion of the target 604 is cumulative, based on the number of beams that are delivered to and through that portion. For example, the portions of the target 604 covered by the beams 605 and 606 receive a total dose that is the sum of the dose delivered by the beam 605 and the dose delivered by the beam 606. In embodiments, the energies of the beams (beam segments) are accurately determined so that, even though the dose along each beam (or beam segment) is not uniform, a uniform cumulative dose distribution is achieved within and across the target 604.

Figure 6C:
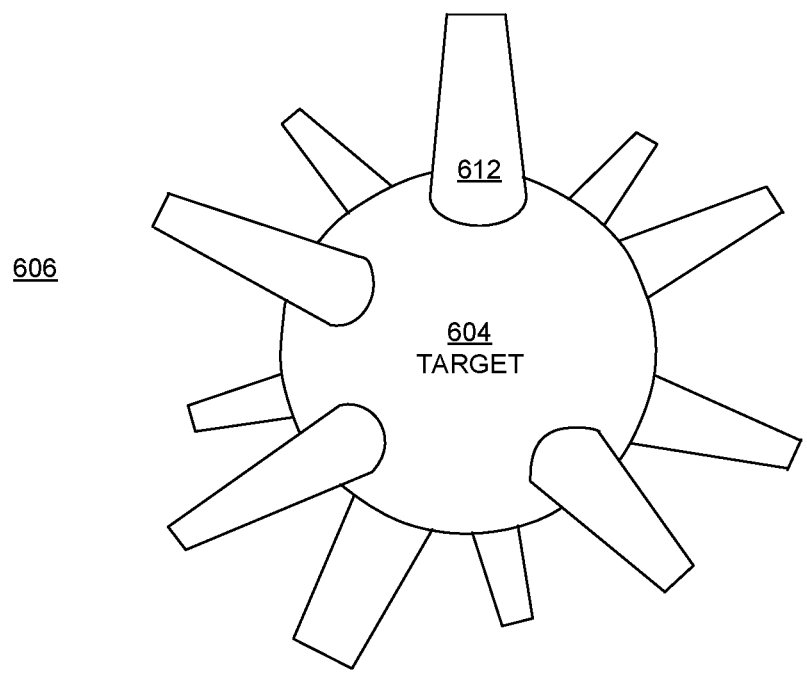
FIG. 6C illustrates a perspective view of an example of a beam geometry in embodiments according to the invention.

FIG. 6C illustrates a perspective view of an example of a beam geometry in embodiments according to the invention. In the example of FIG. 6C, the beams (exemplified by beam 612) are in different planes. As described herein, each beam can include one or more beam segments or beam lets. In this example, the beams' paths overlap only within the target 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver doses sufficient for FLASH RT.

Figure 6D:
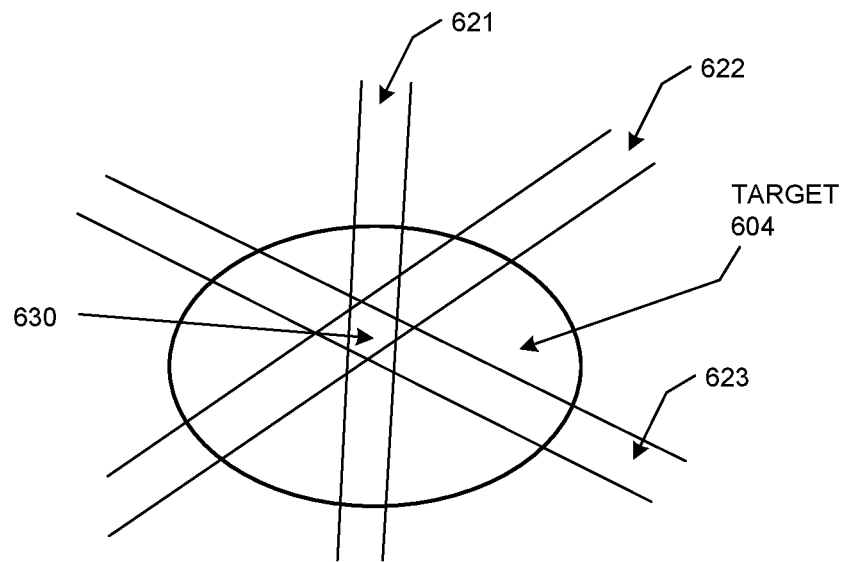
FIG. 6D illustrates a cross-sectional view of an example of a beam geometry in embodiments according to the invention.

FIG. 6D illustrates a cross-sectional view of an example of a beam geometry in embodiments according to the invention. In this example, the beams (exemplified by beams 621, 622, and 623) overlap only within the target and are in the same plane. While three beams are illustrated, the invention is not so limited. As described herein, each beam can include one or more beam segments or beamlets. In this example, the beams' paths overlap only within the target 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver doses sufficient for FLASH RT.

In the example of FIG. 6D, the beams 621, 622, and 623 intersect at the sub-volume 630, other sub-volumes in the target 604 receive doses from two of the beams, other sub-volumes in the target receive doses from only one of the beams, and yet other sub-volumes do not receive a dose. The directions and/or numbers of beam can be varied over a number of treatment sessions (that is, fractionated in time) so that a uniform dose is delivered across the target.

As mentioned above, for implementations that use proton beams or ion beams, the dose delivered by each beam at the respective proximal portion (or edge) of the target 604 may be different from (e.g., less than) the dose delivered by that beam at the respective distal portion (or edge) of the target (as before, proximal and distal are with reference to the source of the beam).

The dose delivered to each portion of the target 604 is cumulative, based on the number of beams that are delivered to and through that portion. Not all beams are depicted in the figures for simplicity; in general, the number of beams is sufficient to achieve a uniform cumulative dose distribution within the target 604.

In general, the surface of a target can be viewed as having a number of discrete facets. From this perspective, for beams other than photon beams, each incident beam is orthogonal to each facet such that the beams do not overlap outside the target. In the case of photon beams, each incident beam is parallel to the facet and does not overlap other beams outside the target.

Figure 7A:
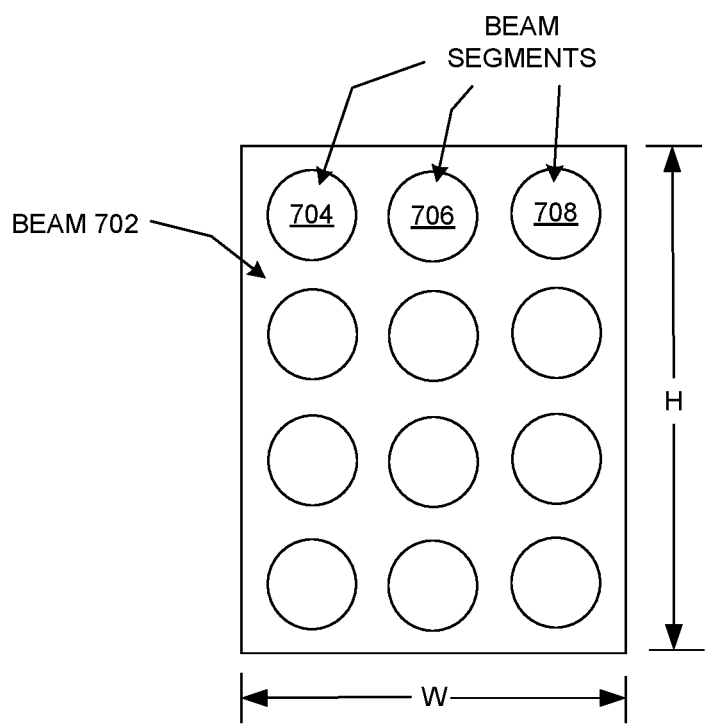
FIG. 7A illustrates a beam's eye view of a beam in embodiments according to the invention.

FIG. 7A illustrates a beam's eye view (BEV) of a beam 702 in embodiments according to the invention. That is, FIG. 7A illustrates a cross-section of a beam. The beams of FIGS. 6A, 6B, 6C, and 6D are examples of the beam 702. The beam 702 is illustrated as being rectangular in shape having a height H and width W. However, the invention is not so limited, and the beam 702 can have virtually any regular or irregular cross-sectional (e.g., BEV) shape. For example, the shape of the beam 702 can be defined using an MLC that blocks a portion or portions of the beam. Different beams can have different shapes.

In the FIG. 7A embodiment, the beam 702 includes a number of beam segments or beam lets (that also may be referred to as spots) exemplified by beam segments 704, 706, and 708. A maximum energy (e.g., 80 MeV) is specified for the beam 702, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The energy per beam segment is defined so that the beam segment will deliver a fraction of the prescribed dose such that, in combination with the other beam segments in the beam, and in combination with the other beams (and beam segments), a uniform (homogeneous) cumulative dose that satisfies the prescribed dose will be delivered within and across the volume of the target. The defined energy level or intensity can be realized for each beam segment using the beam energy adjuster 407 of FIG. 4A.

Each beam segment can deliver a relatively high dose in a relatively short period of time. For example, each beam segment can deliver at least 4 Gy in less than one second, and may deliver as much as 20 Gy or 50 Gy or more in less than one second. The energy or intensity of each beam segment can be controlled using the beam energy adjuster 407 of FIG. 4A so that the beam segment has sufficient energy to reach the distal edge of the target.

In operation, in embodiments, the beam segments are delivered sequentially. For example, the beam segment 704 is delivered to the target (turned on) and then turned off, then the beam segment 706 is turned on then off, then the beam segment 708 is turned on then off, and so on. Each beam segment may be turned on for only a fraction of a second (on the order of milliseconds).

Figure 7B:
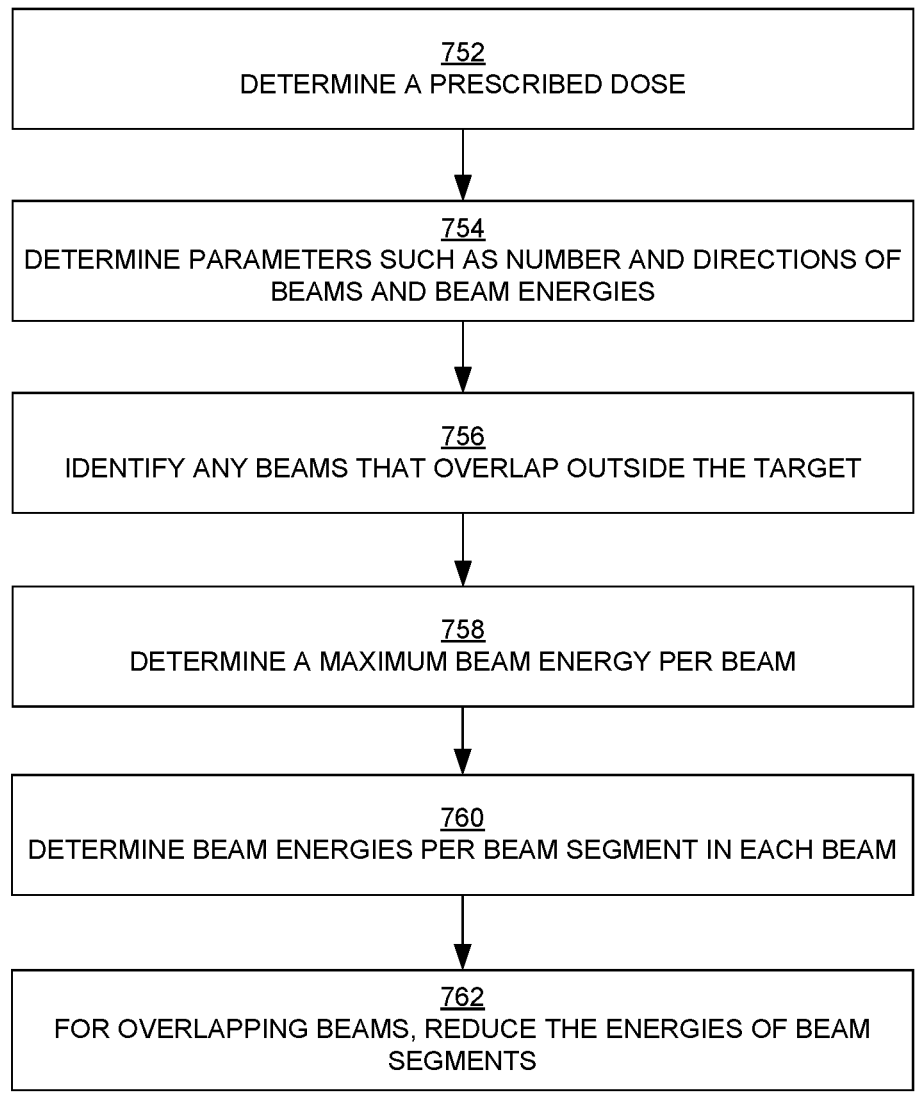
FIG. 7B is a flowchart of an example of computer-implemented operations for weighting beam segments during radiation treatment planning in embodiments according to the present invention.

FIG. 7B is a flowchart 750 of an example of computer-implemented operations for weighting beam segments during radiation treatment planning in embodiments according to the present invention. The flowchart 750 can be implemented as computer-executable instructions (e.g., the optimizer model 150 of FIG. 3) residing on some form of computer-readable storage medium (e.g., using the computing system 100 of FIG. 1).

Embodiments according to the invention introduce an additional parameter during weighting of the beam segments in the beams (also referred to as spot weighting), depending on whether a beam overlaps another beam outside the target.

In block 752 of FIG. 7B, a prescribed dose to be delivered into and across a target is determined. The prescribed dose can be generated using the system 300 of FIG. 3.

In block 754 of FIG. 7B, values of parameters such as the number of beams to be directed into sub-volumes in the target, directions of the beams, and beam energies are accessed. As described above, the beams' paths overlap inside the target. These parameter values can be generated using the system 300 of FIG. 3.

In block 756 of FIG. 7B, any beams that overlap outside the target are identified.

In block 758, for each beam, a maximum beam energy for the beam is determined.

In block 760, for each beam, beam energies for the beam segments are determined as a percentage of the maximum beam energy for the beam.

In block 762, for each overlapping beam identified in block 756, the beam energies for the beam segments of those beams are reduced by a respective factor. The factor can be increased (to increase the amount of reduction) for a beam that intersects more than one other beam. In other words, the penalty is greater if normal (healthy) tissue is hit by more than one beam. The factors applied to the beam energies for these beam segments are determined such that the cumulative dose delivered to the target satisfies the prescribed dose. In this manner, the beam energies or intensities and the associated doses for beams that overlap outside the target are reduced while still allowing the prescribed dose to be delivered to the target.

Figure 7C:
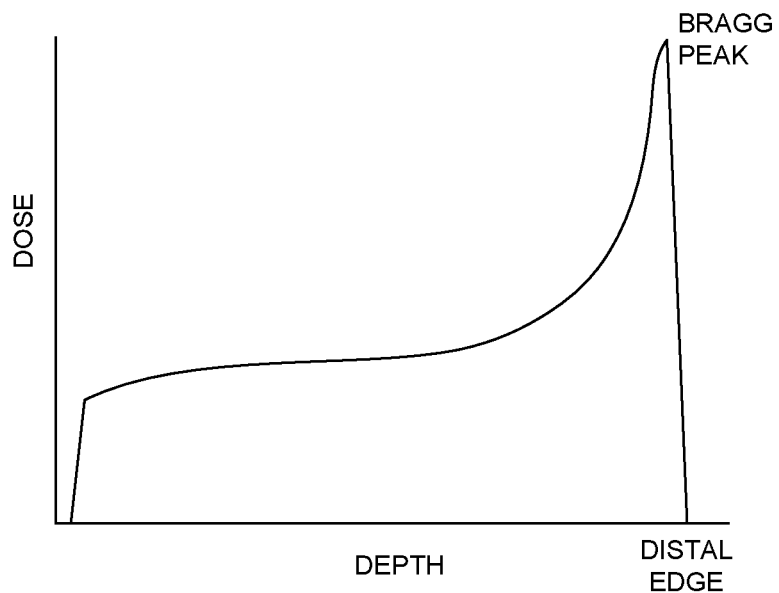
FIG. 7C is an example of a depth dose curve for a beam segment in embodiments according to the invention.

FIG. 7C is an example of a depth dose curve for a beam segment for a beam such as a proton beam or an ion beam that has a Bragg peak in embodiments according to the invention. The example of FIG. 7C shows calculated dose level as a function of depth in the target (distance from the beam source) for the beam 702 or for any of the beam segments in the beam. The energy level or intensity of each beam segment can be controlled using the beam energy adjuster 407 (FIG. 4A) such that the Bragg peak is in the portion at (adjacent to or near) the distal edge of the target as shown in FIG. 7C.

With reference back to FIG. 6B, it can be seen (or deduced) that greater portions of each beam overlap toward the center of the target 604 than at the edges of the target, and more beams overlap at or near the center of the target 604 than at the edges of the target. For example, the beams 602 and 603 do not overlap at the proximal edge 608 of the target 604, overlap more toward the center of the target, overlap completely at or near the center of the target, and overlap partially past the center and at the distal edge 610. All beams overlap at the center of the target 604, but all beams do not overlap at the edges of the target. As mentioned previously herein, the dose contributed by each beam is cumulative, and the target 604 can be represented by the 3D elements known as voxels or sub-volumes. Each voxel or sub-volume will receive radiation from one or more beam segments delivered from different directions. The total dose for a voxel is the sum of the doses delivered by each beam segment received by the voxel. By shaping the beam segments as shown in the example of FIG. 7C for beams (e.g., proton beams and ion beams) that have a Bragg peak, the portions or voxels or sub-volumes in the target 604 that are traversed by fewer beams (beam segments) will receive a larger dose per beam segment because the Bragg peaks of those beam segments coincide with the locations of those portions/voxels/sub-volumes, while the portions/voxels/ sub-volumes in the target that are traversed by more beams (beam segments) will receive a smaller dose per beam segment because the Bragg peaks of the latter beam segments do not coincide with the locations of the latter portions/voxels. In other words, the Bragg peak of each beam is at the distal edge of the target 604, where there is less overlap between beams, and the dose per beam is less than the Bragg peak at locations inside the target where there is more overlap between beams. In this manner, for embodiments that use beams that have Bragg peaks, a uniform dose can be delivered within and across the target 604.

Figure 7D:
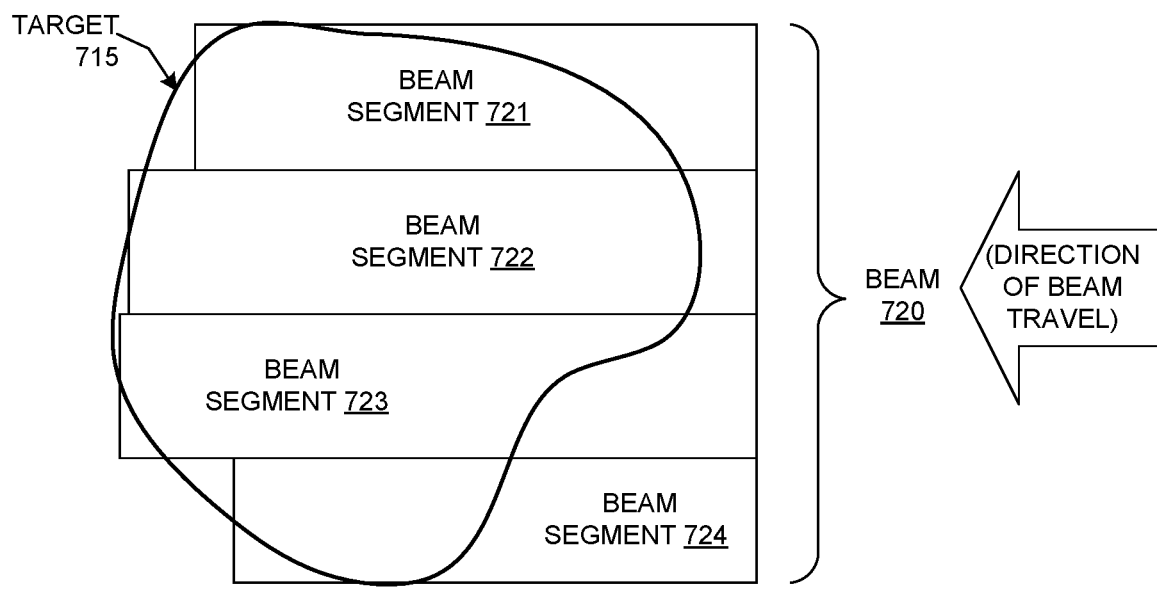
FIG. 7D illustrates a cross-sectional view of a target and a beam including beam segments in embodiments according to the invention.

FIG. 7D illustrates a cross-sectional view of an irregularly shaped target 715 and a beam 720 that includes four beam segments 721, 722, 723, and 724 in the longitudinal direction in embodiments according to the invention. As described above, the energy of each of the beam segments 721, 722, 723, and 724 can be individually defined and independently controlled (e.g., using the beam energy adjuster 407 of FIG. 4A) so that the beam segment has sufficient energy to reach the distal edge of the target 715. In particular, for beams like proton beams and ion beams that have Bragg peaks, the energy level of the beam segments 721, 722, 723, and 724 can be independently controlled using the beam energy adjuster 407 such that the Bragg peak of each beam segment is in the portion at (adjacent to or near) the distal edge of the target 715. In this manner, the range of the beam 720 can be shaped so that it follows the shape of the target 715 in the longitudinal direction. The cross-sectional size (e.g., height and width or diameter) of each beam segment can be specified according to the complexity of the shape of the target 715. For example, if the target surface is relatively uniform (e.g., flat), then the size of the beam segment can be larger.

Figure 8A:
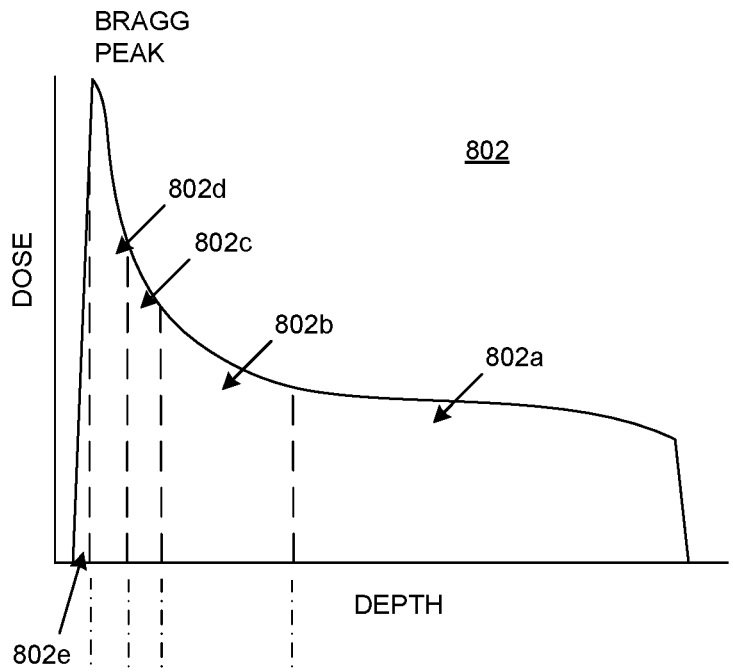
FIG. 8A is an example of a depth dose curve for a beam in embodiments according to the invention.
Figure 8B:
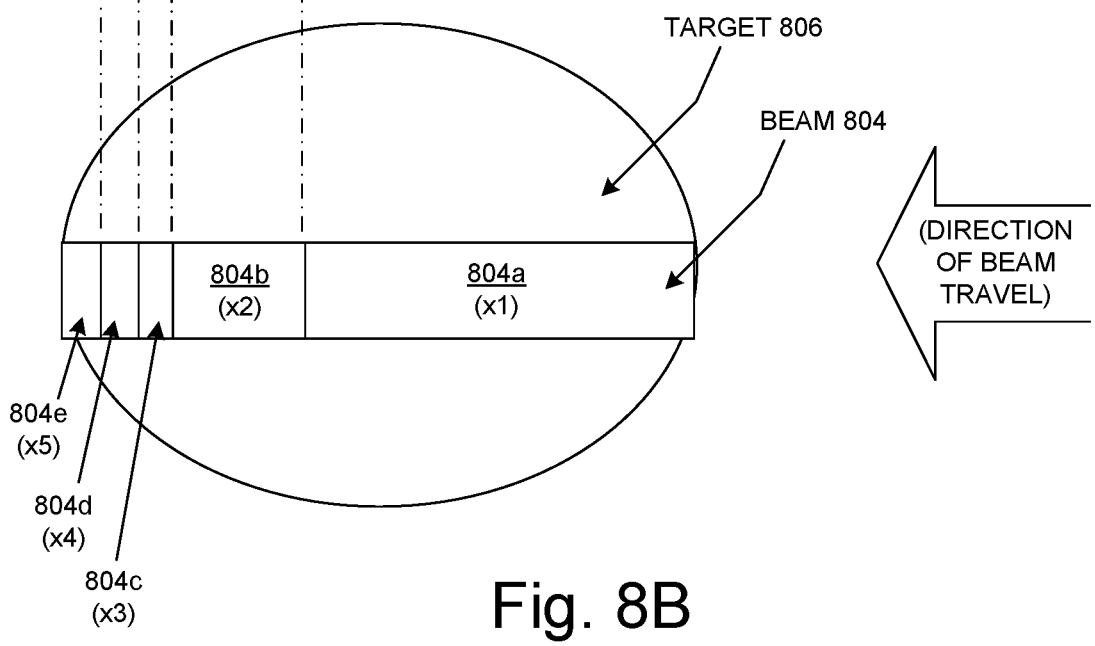
FIGS. 8B, 8C, and 8D illustrate beams in a portion of a target in embodiments according to the invention.

FIG. 8A is an example of a depth dose curve 802 for a beam 804 in embodiments according to the invention. The example of FIG. 8A shows calculated dose level as a function of depth in a target 806 (distance from the beam source) for the beam 804. In the example of FIG. 8A, the beam 804 is a beam that has a Bragg peak (e.g., a proton beam or an ion beam). FIG. 8B illustrates the beam 804 in a portion of the target 806 in embodiments according to the invention. The following discussion presents examples in the context of a beam; however, as described above, a beam can include beam segments, and the examples and discussion below can be readily extended to beam segments.

In the example of FIG. 8A, the depth dose curve 802 is divided into a set of regions 802a, 802b, 802c, 802d, and 802e (802a-e). In corresponding fashion, the beam 804 is divided into a set of longitudinal beam regions 804a, 804b, 804c, 804d, and 804e (804a-e). The beam regions 804a-e are aligned with the regions 802a-e. The widths of the regions 802a-e (and hence the lengths of the beam regions 804a-e) increase in size as the distance from the Bragg peak increases because that is where the calculated dose is more homogeneous (where the dose curve is relatively flat). At and near the Bragg peak (e.g., the regions 802c, 802d, and 802e), the regions are shorter/thinner.

Each of the beam regions 804a-e is assigned a value xn (n=1, 2, . . . , 5 in the example) that corresponds to the calculated amount of dose for the beam region. The region 804a has a value of x1, the region 804b has a value x2, and so on. For example, the values xn may range from one (1) to 100. In embodiments, the values are generally proportional to the amount of calculated dose. In one or more such embodiments, the value x4 for the beam region 804d corresponding to the location 802d of the Bragg peak in the depth dose curve 802 is the largest value, greater than the other values assigned to the other beam regions in the beam 804.

In FIG. 8B, the beam 804 is shown entering the target 806 from a certain direction. If the beam 804 enters the target 806 from a different direction, then the values xn may be different. In other words, the values xn may be different depending on the gantry angle or beam direction associated with the beam 806 even if the beam energy does not change with angle or direction. In embodiments, values are assigned to the beam regions 804a-e depending on both the corresponding dose depth curve 802 and the beam direction.

Figure 8C:
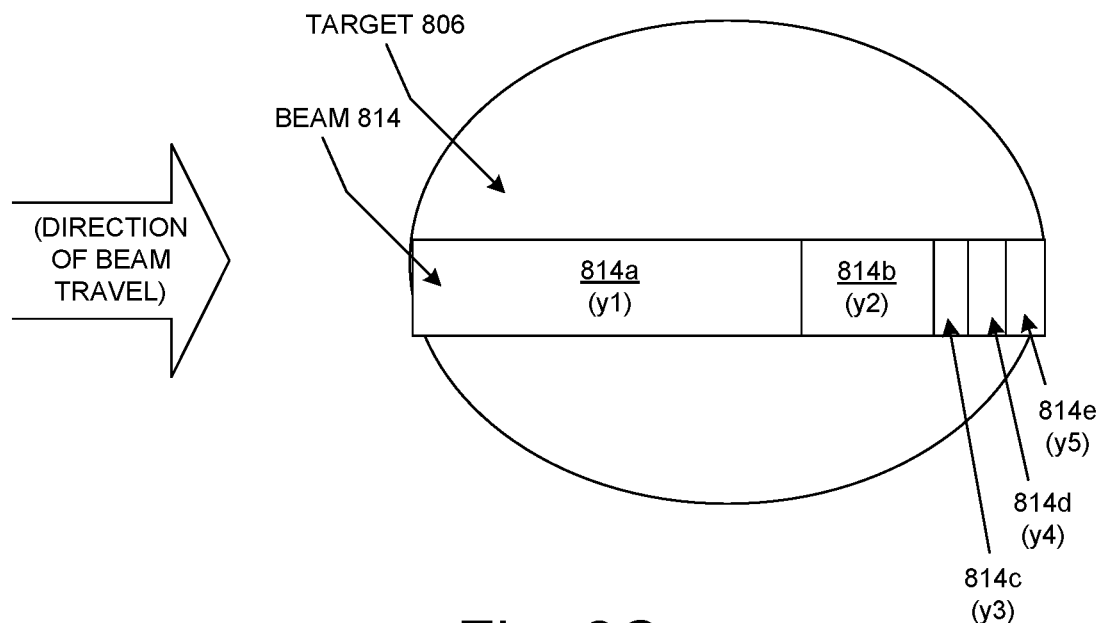

FIG. 8C shows a second beam 814 that passes through the target along the same path as the beam 804 but in the opposite direction in embodiments according to the invention. That is, paths of the beams 804 and 814 overlap as in the example of FIG. 6B. In the present embodiments, the beam 814 is a beam that has a Bragg peak (e.g., a proton beam or an ion beam). The beams 804 and 814 are not necessarily delivered at the same time although they can be.

Like the beam 804, the beam 814 is divided into a set of longitudinal beam regions 814a, 814b, 814c, 814d, and 814e (814a-e) that are aligned with regions of a dose depth curve (not shown) for the beam 814. Each of the beam regions 814a-e is assigned a value yn (n=1, 2, . . . , 5 in the example) that corresponds to the calculated amount of dose for the beam region. The values yn may range from 1 to 100. In embodiments, the values at the radiation isocenter for the beams 804 and 814 are the same.

Figure 8D:
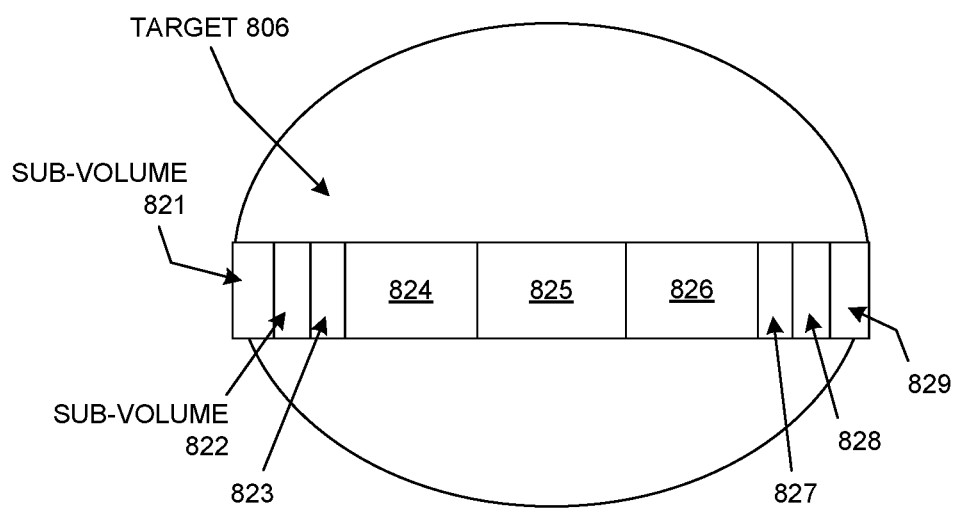

When beams overlap in the target 806, the sub-volumes of the target traversed by the beams receive a dose from each beam. In the examples of FIGS. 8B and 8C, the cumulative dose for a sub-volume is represented by adding together the values of xn and yn corresponding to the regions of the beams 804 and 814 that traverse the sub-volume. FIG. 8D shows both beams 804 and 814 in overlapping fashion. In the example of FIG. 8D, the sub-volume 821 has a cumulative dose represented by x1+y5, the sub-volume 822 has a cumulative dose represented by 824 has a cumulative dose represented by x4+y5, the sub-volume 825 has a cumulative dose represented by x5+y5, the sub-volume 826 has a cumulative dose represented by x5+y4, the sub-volume 827 has a cumulative dose represented by x5+y3, the sub-volume 828 has a cumulative dose represented by x5+y2, and the sub-volume 829 has a cumulative dose represented by x5+y1.

As shown in FIG. 6B, a sub-volume can be traversed by more than two beams, in which case the cumulative dose for the sub-volume is represented by adding the appropriate value for each beam that reaches the sub-volume. That is, a total value is determined for each sub-volume in the target 806 by adding together the values for each beam region of each beam that reaches the sub-volume.

The optimizer model (FIG. 3) can adjust the parameters that affect the calculated doses delivered to the target 806 to achieve a satisfactorily uniform cumulative dose across the target 806. A satisfactorily uniform cumulative dose is indicated when all the total values per sub-volume in the target 806 are the same or when the differences between the total values per sub-volume satisfy a threshold value. The threshold value can be, for example, a value that specifies the maximum amount of difference between total values that is permitted. That is, the parameters that affect the calculated doses to be delivered by the beam regions are adjusted until the total values for the sub-volumes are all within a specified range of each other or are the same, thereby indicating that the dose to be delivered across the target is satisfactorily uniform.

Figure 9:
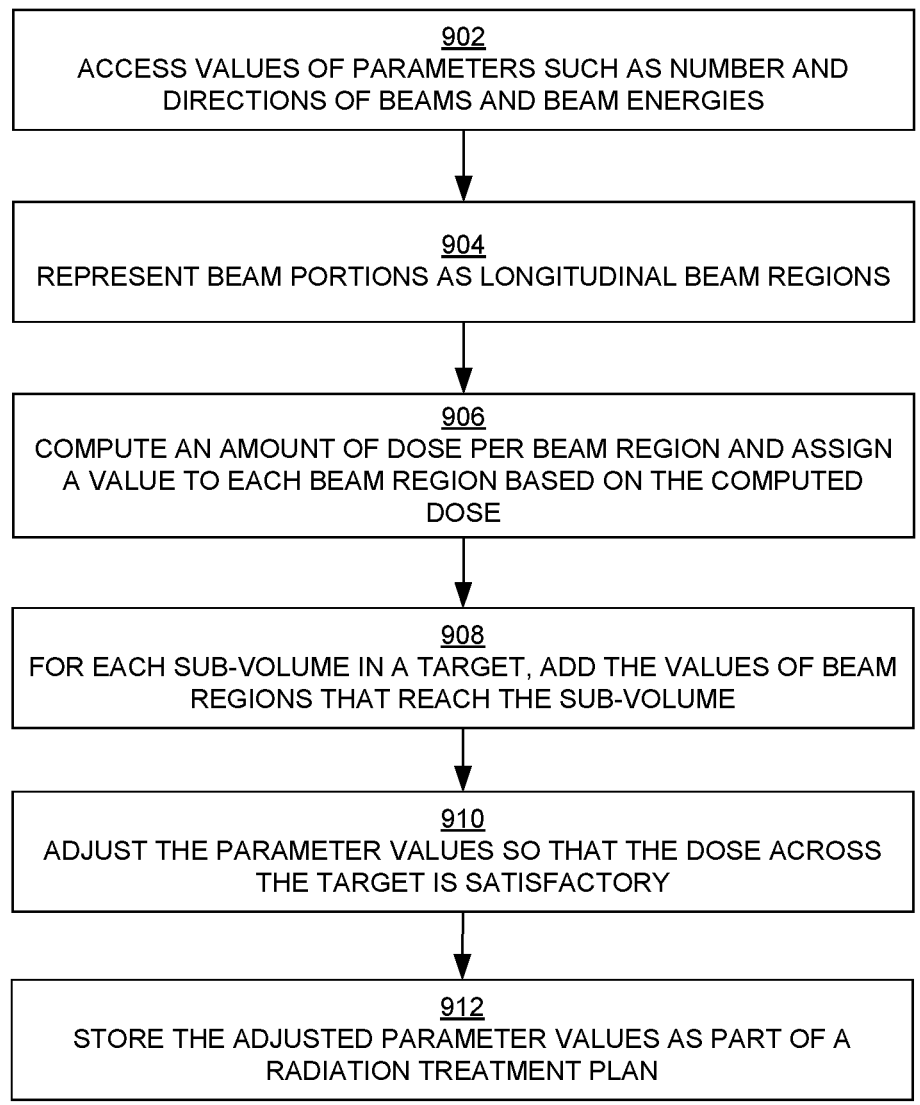
FIG. 9 is a flowchart of an example of computer-implemented operations for generating a radiation treatment plan in embodiments according to the present invention.

FIG. 9 is a flowchart 900 of an example of computer-implemented operations for generating a radiation treatment plan in embodiments according to the present invention. The flowchart 900 can be implemented as computer-executable instructions (e.g., the optimizer model 150 of FIG. 3) residing on some form of computer-readable storage medium (e.g., using the computing system 100 of FIG. 1).

In block 902 of FIG. 9, values of parameters such as a number of beams to be directed into and across sub-volumes in a target, directions of the beams, and beam energies for the beams, are accessed. These parameter values can be generated using the system 300 of FIG. 3 and may be stored in a memory of the computing system 100 of FIG. 1.

In block 904 of FIG. 9, each portion of the beams that is in the target is represented as a respective set of longitudinal beam regions. See, for example, FIG. 8B and the discussion thereof.

In block 906, an amount of dose to be delivered by each of the beam regions is computed and a value is assigned to each beam region corresponding to the computed amount of dose for the beam region. See, for example, FIGS. 8B and 8C and the discussion thereof.

In block 908 of FIG. 9, for each sub-volume in the target, the value for each beam region of each beam that reaches the sub-volume are added together to generate a total value for the sub-volume. See, for example, FIG. 8D and the discussion thereof.

In block 910 of FIG. 9, the values of the parameters that affect the calculated amounts of dose to be delivered by the beam regions are adjusted until differences between the total values for the sub-volumes satisfy a threshold value or are the same (in the latter case, the threshold value is zero). That is, the values of the parameters are adjusted until the dose across the target is satisfactory (e.g., it is uniform or nearly uniform across the entire target).

In block 912, the adjusted parameter values are stored in memory of the computing system 100 (FIG. 1) as part of the radiation treatment plan 322 (FIG. 3).

In embodiments according to the invention, a dose threshold is used to specify limits for the radiation treatment plan. Examples of dose thresholds are presented in FIGS. 10A and 10B.

Figure 10A:
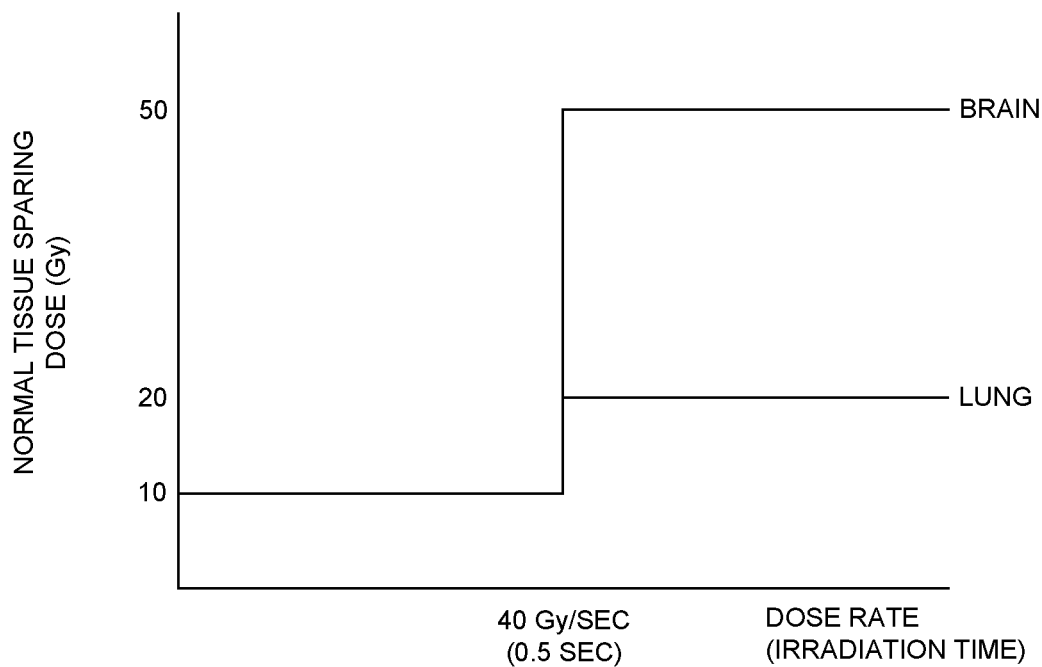
FIGS. 10A and 10B are examples of dose thresholds in embodiments according to the present invention.
Figure 10B:
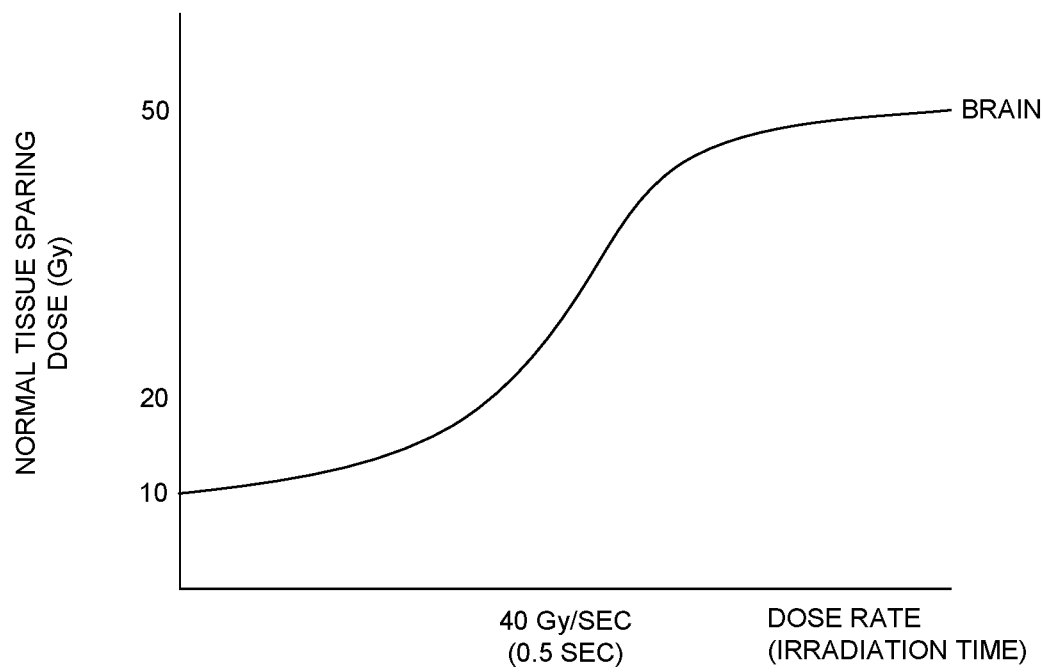

FIGS. 10A and 10B show normal (healthy) tissue sparing-dose as a function of dose rate or irradiation time. In the example of FIG. 10A, the function is a step-wise function. In the example of FIG. 10B, the function is sigmoidal. Doses, dose rates, and irradiation times in FIGS. 10A and 10B are only examples. Other functions can be used. The dose threshold curves can be tissue-dependent. For instance, the dose threshold curve for the lungs may be different from that for the brain. The appropriate dose threshold curve(s) can be utilized in the optimization model 150 (FIG. 3) to establish dose limits for radiation treatment planning. For example, the appropriate (e.g., tissue-dependent) dose threshold curve can be used to determine beam directions (gantry angles) and beam segment weights (FIG. 7A). That is, parameters that affect dose can be adjusted during radiation treatment planning so that the limits in the dose threshold curve are satisfied.

Dose limits can include, but are not limited to: a maximum limit on irradiation time for each sub-volume (voxel) in the target (e.g., for each voxel of target tissue, treatment time less than x1 seconds); a maximum limit on irradiation time for each sub-volume (voxel) outside the target (e.g., for each voxel of normal tissue, treatment time less than x2 seconds; x1 and x2 may be the same or different); a minimum limit on dose rate for each sub-volume (voxel) in the target (e.g., for each voxel of target tissue, dose rate greater than y1 Gy/sec); and a minimum limit on dose rate for each sub-volume (voxel) outside the target (e.g., for each voxel of normal tissue, dose rate greater than y2 Gy/sec; y1 and y2 may be the same or different). In general, the limits are intended to minimize the amount of time that normal tissue is irradiated.

Figure 11:
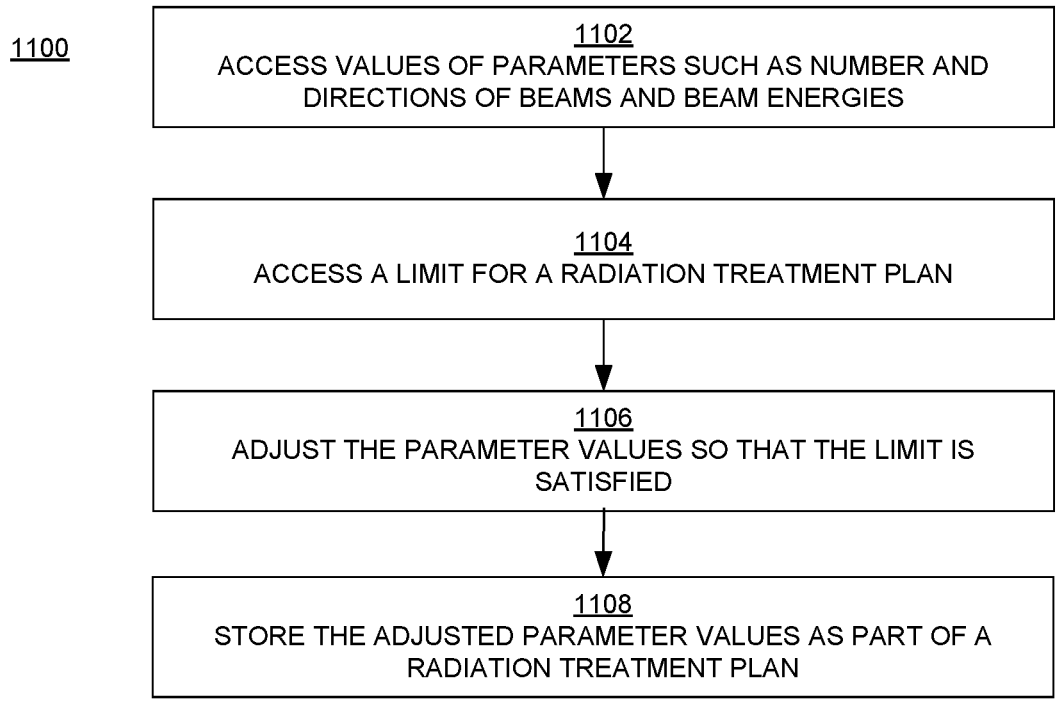
FIG. 11 is a flowchart of an example of computer-implemented operations for radiation treatment planning in embodiments according to the present invention.

FIG. 11 is a flowchart 1100 of an example of computer-implemented operations for radiation treatment planning in embodiments according to the present invention. The flowchart 1100 can be implemented as computer-executable instructions (e.g., the optimizer model 150 of FIG. 3) residing on some form of computer-readable storage medium (e.g., using the computing system 100 of FIG. 1).

In block 1102 of FIG. 11, values of parameters such as number of beams to be directed into sub-volumes in a target, directions of the beams, and beam energies are accessed. These parameter values can be generated using the system 300 (FIG. 3) and may be stored in a memory of the computing system 100 (FIG. 1).

In block 1104 of FIG. 11, information that specifies limits for the radiation treatment plan is accessed. In embodiments, the limits are based on a dose threshold (see FIGS. 10A and 10B, for example), and include a maximum limit on irradiation time for each sub-volume outside the target. Other limits can include a maximum limit on irradiation time for each sub-volume in the target, a minimum limit on dose rate for each sub-volume in the target, and a minimum limit on dose rate for each sub-volume outside the target.

In block 1106 of FIG. 11, in embodiments, the values of the parameters are adjusted until the irradiation time for each sub-volume outside the target satisfies the maximum limit on irradiation time. In general, the goal is to minimize the amount of time healthy tissue (tissue outside the target) is being irradiated. Note that multiple beams may pass through a sub-volume outside the target, as long as the total irradiation time for that sub-volume is less than the limit.

In embodiments, the values of the parameters that affect calculated amounts of dose to be delivered by the beams are adjusted until calculated total doses for the sub-volumes in the target are within a specified range of each other. In other words, the values of the parameters that affect calculated amounts of dose to be delivered by the beams are adjusted until calculated total doses for the sub-volumes in the target are satisfactorily uniform across the entire target.

In block 1112, adjusted parameter values are stored in a memory of the computing system 100 (FIG. 1) as part of the radiation treatment plan 322 (FIG. 3).

As previously discussed herein, beam directions (gantry angles) are defined such that the amount of overlap between beam paths is minimized outside the target. The goal is have no overlap between beam paths outside the target; however, that may not always be possible or advantageous from the perspective of treating the target.

Figure 12:
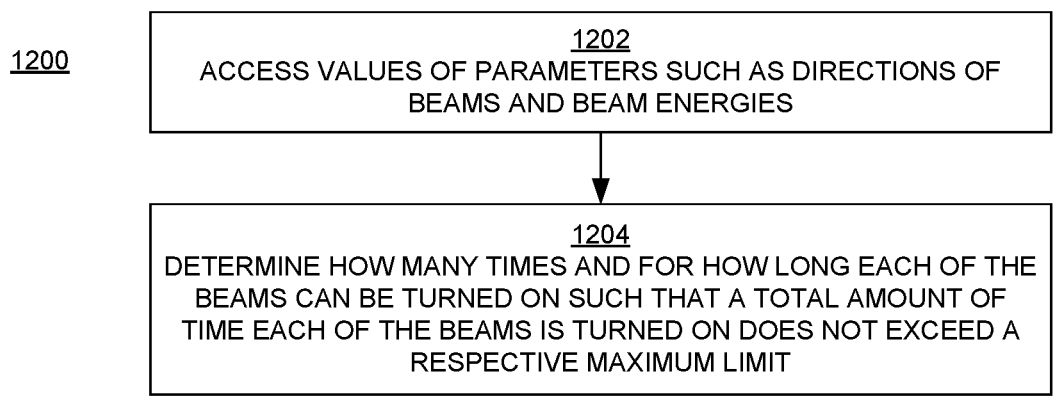
FIG. 12 is a flowchart of an example of computer-implemented operations for radiation treatment planning in embodiments according to the present invention.

FIG. 12 is a flowchart 1200 of an example of computer-implemented operations for radiation treatment planning in embodiments according to the present invention. The flowchart 1200 can be implemented as computer-executable instructions (e.g., the optimizer model 150 of FIG. 3) residing on some form of computer-readable storage medium (e.g., using the computing system 100 of FIG. 1).

In block 1202 of FIG. 12, values of parameters such as number of beams to be directed into sub-volumes in a target and/or directions of the beams and beam energies are accessed. These parameter values can be generated using the system 300 of FIG. 3 and may be stored in a memory of the computing system 100 of FIG. 1. The beam energies and number and/or directions of the beams are determined such that the entire target receives a minimum prescribed dose.

In block 1204 of FIG. 12, the number of times (how many times) each of the beams can be turned on is determined, and the amount of time (how long) a beam can be turned on each time the beam is turned on is also determined, such that the total amount of time that a beam is turned on does not exceed a maximum limit for that beam (e.g., the beam's "on time" can be minimized).

Note that, as previously mentioned herein, a sub-volume outside the target may be irradiated by only one beam, or it may be irradiated by multiple beams (two or more beams may overlap the sub-volume). Thus, a sub-volume outside the target may be irradiated multiple times: the sub-volume may be irradiated multiple times by the same beam (that beam is turned on and off multiple times), or the sub-volume may be irradiated by multiple beams (each of those beams may be turned on and off once or turned on and off multiple times). However, the total amount of time that a sub-volume can be irradiated is minimized. That is, a maximum limit for irradiation time is specified per sub-volume. Equivalently, a maximum limit on the total amount of time each beam can be turned on is specified. Thus, the total amount of time each beam is turned on can be minimized while still satisfying the prescribed dose to be delivered to the target. In this manner, a total amount of time each sub-volume outside the target is irradiated by the beams does not exceed a maximum limit (e.g., it can be minimized) and, therefore, a total amount of dose delivered to each sub-volume outside the target does not exceed a maximum limit (e.g., it can be minimized), while still delivering the prescribed dose across the entire target.

Figure 13:
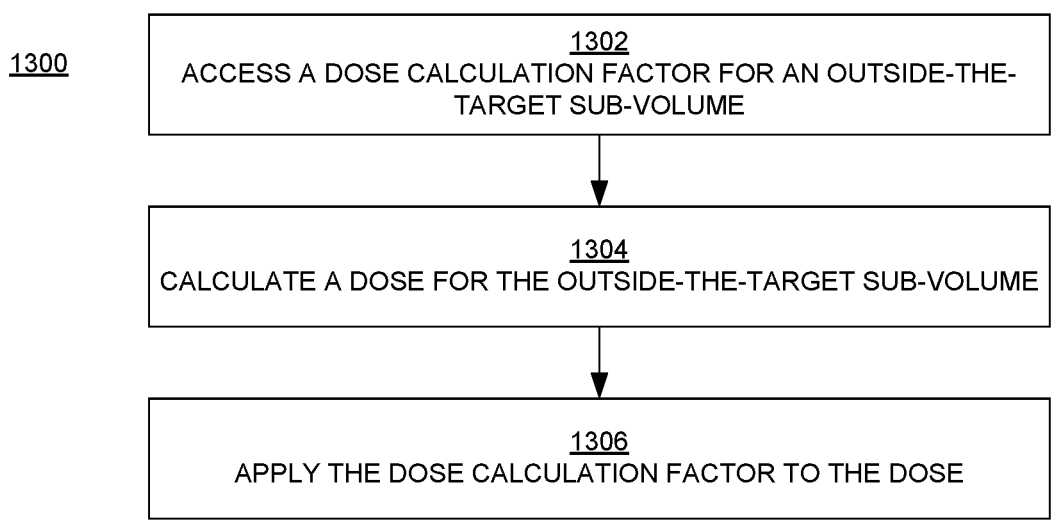
FIG. 13 is a flowchart of an example of computer-implemented operations for calculating doses during radiation treatment planning in embodiments according to the present invention.

FIG. 13 is a flowchart 1300 of an example of computer-implemented operations for calculating doses, in particular a dose calculation for an outside-the-target sub-volume, during radiation treatment planning in embodiments according to the present invention. Significantly, as will be seen, the methodology of the flowchart 1300 accounts for the tissue-sparing effects of FLASH RT on normal (healthy) tissue. The flowchart 1300 can be implemented as computer-executable instructions (e.g., the optimizer model 150 of FIG. 3) residing on some form of computer-readable storage medium (e.g., using the computing system 100 of FIG. 1).

In block 1302 of FIG. 13, a value for a dose calculation factor for the outside-the-target sub-volume is accessed. The value for the dose calculation factor is determined according to how many beams reach the outside-the-target sub-volume. If a single beam reaches the outside-the-target sub-volume, then the dose calculation factor has a first value that is close to zero (e.g., 0.1). If the outside-the-target sub-volume is reached by more two beams, then the value of the dose calculation factor is increased (e.g., to 0.3). The dose calculation factor is increased as the number of beams received by the outside-the-target sub-volume increases. If the outside-the-target volume receives all beams specified in the radiation treatment plan, then the dose calculation factor is 1.0, thus reflecting that the tissue-sparing effects of FLASH RT are not realized.

In block 1304, a dose for the outside-the-target sub-volume is calculated.

In block 1306, the value of the dose calculation factor is applied to the dose calculated for the outside-the-target sub-volume. That is, for example, the calculated dose is multiplied by the dose calculation factor. If, for example, a single beam is received by the sub-volume, then the calculated dose is reduced by a factor of 0.1, thus recognizing the tissue-sparing effects of FLASH RT.

In summary, embodiments according to the invention improve radiation treatment planning and the treatment itself by expanding FLASH RT to a wider variety of treatment platforms and target sites. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified. Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to IMRT and IMPT, embodiments according to the invention can be used in spatially fractionated radiation therapy including high-dose spatially fractionated grid radiation therapy and microbeam radiation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method of radiation treatment planning, the method comprising:
  accessing values of parameters from memory of a computing system, wherein the parameters comprise a number of beams to be directed into sub-volumes in a target, directions of the beams, and beam energies for the beams;
  accessing information that specifies limits for the radiation treatment plan, and wherein the limits comprise a minimum limit on dose rate for each sub-volume in the target;
  adjusting the values of the parameters until a dose rate for each sub-volume inside the target satisfies the minimum limit on dose rate; and
  storing the values of the parameters after said adjusting in the memory of the computing system as at least a part of the radiation treatment plan.

2. The method of claim 1, wherein each portion of the beams that is in the target is represented as a respective set of longitudinal beam regions, and wherein the method further comprises:
  for each of the beam regions, computing a dose rate to be delivered by a beam region and assigning a value to the beam region corresponding to the dose rate; and
  for each of the sub-volumes in the target, computing a total value for the sub-volume by adding together the value for each beam region of each beam that reaches the sub-volume;
  wherein said adjusting further comprises adjusting the parameters that affect calculated dose rates to be delivered by the beam regions until differences between respective total values for the sub-volumes in the target satisfy a threshold value.

3. The method of claim 1, wherein said adjusting further comprises:

determining whether a beam overlaps any other beams outside the target; and weighting beam intensities for beam segments of the beam according to how many other beams are overlapped by the beam outside the target.

4. The method of claim 1, further comprising performing a dose calculation for an outside-the-target sub-volume, wherein said performing a dose calculation comprises:

accessing a value for a dose calculation factor for the outside-the-target sub-volume, wherein the value for the dose calculation factor is determined according to how many beams reach the outside-the-target sub-volume;

calculating a dose for the outside-the-target sub-volume; and applying the value of the dose calculation factor to the dose calculated for the outside-the-target sub-volume.

5. The method of claim 4, wherein the dose calculation factor reduces the dose calculated for the outside-the-target sub-volume if only one beam reaches the outside-the-target sub-volume.

6. The method of claim 1, wherein the limits further comprise a limit selected from the group consisting of: a maximum limit on irradiation time for each sub-volume outside the target; and a minimum limit on dose rate for each sub-volume outside the target.

7. The method of claim 1, wherein the limits are based on a dose threshold, and wherein the dose threshold is dependent on tissue type.

8. The method of claim 1, wherein the beams comprise a type of beam selected from the group consisting of: proton; electron; photon; atom nuclei; and ion.

9. The method of claim 1, further comprising adjusting the values of the parameters that affect calculated dose rates to be delivered by the beams until calculated total dose rates for the sub-volumes in the target are each within a specified range.

10. A computer-implemented method of radiation treatment planning, the method comprising:

accessing a value of a prescribed dose to be delivered into and across a target volume; and determining directions of beams of radiation to be directed into the target volume, wherein said determining comprises determining directions wherein an amount of overlap between portions of the beams outside the target volume is less than a threshold value and wherein a predicted dose delivered by the beams satisfies the value of the prescribed dose.

11. The method of claim 10, wherein the threshold value is zero.

12. The method of claim 10, wherein the amount of overlap is a total amount of overlap of all of the portions of the beams outside the target volume.

13. The method of claim 10, wherein the amount of overlap is a total amount of overlap of all of the portions of the beams outside the target volume, wherein at least some of the beams overlap within the target volume, and wherein the threshold value is a total amount of overlap of portions of the beams that overlap within the target volume.

14. The method of claim 10, wherein the beams comprise a type of beam selected from the group consisting of: proton; electron; photon; atom nuclei; and ion.

15. The method of claim 10, wherein regions outside the target volume comprise a plurality of sub-volumes, and wherein each sub-volume of the plurality of sub-volumes outside the target volume is not intersected by more than two of the beams.

16. A computer-implemented method of radiation treatment planning, the method comprising:

accessing values of parameters, the values comprising a number of beams to be directed into sub-volumes in a target; and determining a number of times each beam of the beams is turned on, and determining an amount of time each beam of the beams is turned on each time said each beam is turned on, to determine a total amount of time that said each beam is turned on, wherein the total amount of time that said each beam is turned on does not exceed a maximum limit for the beam.

17. The method of claim 16, further comprising:

determining directions of the beams; and determining energies of the beams.

18. The method of claim 17, wherein the energies of the beams, the number of the beams, and the directions of the beams are determined such that a minimum prescribed dose is received across the target.

19. The method of claim 18, wherein the target comprises a plurality of voxels, and wherein the minimum prescribed dose comprises a dose value for each voxel of the plurality of voxels.

20. The method of claim 16, wherein the beams comprise a type of beam selected from the group consisting of: proton; electron; photon; atom nuclei; and ion.

* * * * *